US008771977B2

(12) United States Patent
Nocker et al.

(10) Patent No.: US 8,771,977 B2
(45) Date of Patent: Jul. 8, 2014

(54) METHOD OF MICROBIAL PROFILING OF A SAMPLE USING PHENANTHRIDIUM DERIVATIVES

(75) Inventors: Andreas Nocker, Utrecht (NL); Anne K. Camper, Bozeman, MT (US)

(73) Assignee: Montana State University, Bozeman, MT (US)

( * ) Notice: Subject to any disclaimer, the term of this patent is extended or adjusted under 35 U.S.C. 154(b) by 0 days.

(21) Appl. No.: 13/470,716

(22) Filed: May 14, 2012

(65) Prior Publication Data
US 2012/0301877 A1 Nov. 29, 2012

Related U.S. Application Data

(62) Division of application No. 12/280,946, filed as application No. PCT/US2007/004922 on Feb. 28, 2007, now Pat. No. 8,198,040.

(60) Provisional application No. 60/776,927, filed on Feb. 28, 2006.

(51) Int. Cl.
*C12Q 1/04* (2006.01)
(52) U.S. Cl.
USPC ............................................ 435/34; 435/6.12
(58) Field of Classification Search
USPC ................................. 435/32, 6.12, 29, 31, 34
IPC .................................. C12Q 1/04,1/689, 1/6806
See application file for complete search history.

(56) References Cited

U.S. PATENT DOCUMENTS

| 5,316,906 | A | 5/1994 | Haugland et al. |
| 5,443,986 | A | 8/1995 | Haughland et al. |
| 6,562,785 | B1 | 5/2003 | Shapiro |
| 8,198,040 | B2 * | 6/2012 | Nocker et al. ................. 435/32 |
| 2003/0203374 | A1 | 10/2003 | Rudi |
| 2009/0123959 | A1 | 5/2009 | Vesper et al. |
| 2009/0305240 | A1 | 12/2009 | Yoshida et al. |
| 2010/0035250 | A1 | 2/2010 | Nocker et al. |

FOREIGN PATENT DOCUMENTS

| WO | WO 01/77379 A2 | 10/2001 |
| WO | WO 2006/007479 A1 | 1/2006 |
| WO | WO 2007/094077 A1 | 8/2007 |
| WO | WO 2007/105965 A1 | 9/2007 |

OTHER PUBLICATIONS

Rudi K et al. Use of Ethidium Monoazide and PCR in Combination for Quantification of Viable and Dead Cells in Complex Samples. Applied and Environmental Microbiology 71(2)1018-1024, Feb. 2005.*
Chang B. et al. Comparison of Ethidium Monoazide and Propidium Monoazide for the Selective Detection of Viable Legionella Cells. Japanese J Infectious Disease 63:119-123, 2010.*
Nocker A. et al. Comparison of Propidium Monoazide with Ethidium Monoazide for Differentiation of Live vs. Dead Bacteria . . . J Microbiological Methods 67:310-320, 2006.*
Nocker A. et al. Molecular Monitoring of Disinfection Efficacy Using Propidium Monoazide in Combination with Quantitative PCR. J Microbiological Methods 70:252-260, 2007.*
Nocker A. et al. Selective Removal of DNA from Dead Cells . . . Applied and Environmental Microbiology 72(3)1997-2004, Mar. 2006.*
Breeuwer et al., "Assessment of viability of microorganisms employing fluorescence Techniques" J. Food. Microbiol. 55:193-200, 2000.
European Patent Office Supplementary Search Opinion based on corresponding European Patent Application No. 07751663.1, mailed on Aug. 19, 2010.
European Search Report, 13 pages, EP appl. No. 12159614.2 (mailed Aug. 3, 2012).
Fukunaga et al., "Production of frameshift mutations in Salmonella by phenanthridinium derivatives: enzymatic activation and photoaffinity labeling", Mutation Research (1984) vol. 127, pp. 31-37.
Hixon et. al., "Selective Covalent Binding of an Ethidium Analog to Mitochondrial DNA with Production of Petite Mutants in Yeast by Photoaffinity Labeling", Journal of Molecular Biology, (1975) vol. 92, pp. 319-329.
International Search Report mailed Jul. 29, 2008 in the International (PCT) Application No. PCT/US2007/04922 which the present application is the U.S. National Stage.
Jenkins et al., "Mutation analysis using the restriction site mutation (RSM) assay," Mut. Res. 405:209-220 (1998).
Nocker et al., "Comparison of Propidium Monoazide for Differentiation of Live vs. Dead Bacteria by Selective Removal of DNA from Dead Cells," J. Micribiol. Meth. 67:310-320 (2006).
Nocker et al., "Selective Removal of DNA from Dead Cells of Mixed Bacterial Communities by Use of Ethidium Monoazide" Appl. Environ. Microbiol. 72:1997-2004, Mar. 2006.
Nogva et al., "Ethidium Monoazide for DNA-Based Differentiation of Viable and Dead Bacteria by 5'-Nuclease PCR" Biotechniques 34:804-808, 2004.
Rudi et al., "Use of Ethidium Monoazide and PCR in Combination for Quantification of Viable and Dead Cells in Complex Samples," Applied and Environmental Microbiology 71(2):1018-1024 (2005).
Rudi et al., "Detection of viable and dead Listeria monocytogenes on gouda-like cheeses by real-time PCR", Lett. Appl. Microbiol. 40:301-306, 2005.
Ruecker et al., "Removal of contaminating DNA from polymerase chain reaction using ethidium monoazide", J. Microbiol. Meth. 68:596-600, Feb 16, 2007.
Third party submission of prior art document in Japanese Application No. 2008-557324, submitted on Jul. 5, 2011 and accepted on Jul. 5, 2011.
English Translation of Third Party Observation filed in EP Application No. 07751663.1 on Jul. 12, 2013.

* cited by examiner

*Primary Examiner* — Ralph Gitomer
(74) *Attorney, Agent, or Firm* — Cooley LLP

(57) ABSTRACT

The present disclosure provides for a method of microbial profiling of a sample using phenanthridium derivatives with a 2+ charge or higher.

10 Claims, 15 Drawing Sheets

A  *E. coli* 0157:H7

B
*Streptococcus sobrinus*

*Salmonella typhimurium*

*Micrococcus luteus*

*Staphylococcus aureus*

METHOD OF MICROBIAL PROFILING OF A SAMPLE USING PHENANTHRIDIUM DERIVATIVES

CROSS REFERENCE TO RELATED APPLICATIONS

This application is a Divisional of U.S. application Ser. No. 12/280,946, filed Aug. 28, 2008, which issued on Jun. 12, 2012 as U.S. Pat. No. 8,198,040, and which is a U.S. National Phase Application of International Application PCT/US2007/004922, filed Feb. 28, 2007, which claims the benefit of U.S. Application No. 60/776,927, filed Feb. 28, 2006, each of which is herein incorporated by reference in its entirety for all purposes.

STATEMENT REGARDING FEDERALLY SPONSORED RESEARCH OR DEVELOPMENT

This research has been supported by a grant (DAAD 19-03-1-0198) from the Army Research Office. Therefore, the U.S. Government has certain rights in this invention.

BACKGROUND

Differentiation of live and dead cells is an important challenge in microbial diagnostics. Metabolic and reproductive activity, and, in the case of pathogenic microorganisms, the potential health risk are limited to the live portion of a mixed microbial population. Four physiological states are distinguished in flow cytometry using fluorescent stains: reproductively viable, metabolically active, intact and permeabilized cells. Depending on the conditions, all stages except the permeabilized cells can have the potential of recovery upon resuscitation and thus have to be considered potentially live[8]. Due to the relatively long persistence of DNA after cell death in the range between days to 3 weeks[4,6], DNA-based diagnostics tend to overestimate the number of live cells. DNA extracted from a sample can originate from cells in any of the four mentioned physiological states including the dead permeabilized cells. Detection of the latter, however, is not desired.

The most important criterion for distinguishing between viable and irreversibly damaged cells is membrane integrity. Sorting out noise derived from membrane-compromised cells helps to assign metabolic activities and health risks to the intact and viable portion of bacterial communities. Live cells with intact membranes are distinguished by their ability to exclude DNA-binding dyes that easily penetrate dead or membrane-compromised cells. This principle is routinely applied for microscopic live-dead discrimination and increasingly in flow-cytometry. The most common membrane-impermeant dye is propidium iodide.

In the last few years, EMA-PCR was reported to be an easy-to-use alternative to microscopic or flow-cytometric distinction between live and dead cells[11,13,14]. This diagnostic DNA-based method combines the use of a live-dead discriminating dye with the speed and sensitivity of real-time PCR. Ethidium monoazide (EMA) is a DNA-intercalating dye with the azide group allowing covalent binding of the chemical to DNA upon exposure to bright visible light (maximum absorbance at 460 nm). Cells are exposed to EMA for 5 minutes allowing the dye to penetrate dead cells with compromised cell walls/membranes and to bind to their DNA. Photolysis of EMA using bright visible light produces a nitrene that can form a covalent link to DNA and other molecules[1,2]. Photo-induced cross-linking was reported to inhibit PCR amplification of DNA from dead cells. In a recent publication it could be shown that EMA-crosslinking to DNA actually rendered the DNA insoluble and led to its loss together with cells debris during genomic DNA extraction[10]. The unbound EMA, which remains free in solution, is simultaneously inactivated by reacting with water molecules[2]. The resulting hydroxylamine is no longer capable of covalently binding to DNA[5]. DNA from viable cells, protected from reactive EMA before light-exposure by an intact cell membrane/cell wall, is therefore not affected by the inactivated EMA after cell lysis. EMA treatment of bacterial cultures comprised of a mixture of viable and dead cells thus leads to selective removal of DNA from dead cells. The species tested were *E. coli* O157:H7[11], *Salmonella typhimurium*[11], *Listeria monocytogenes*[11,13,14] and *Campylobacter jejuni*[13]. These studies did not examine, however, the selective loss of DNA from dead cells.

Though this technique is promising, the use of EMA prior. DNA extraction was found to suffer from a major drawback. In the case of *E. coli* O157:1-17, though the entire genomic DNA from dead cells was removed, the treatment also resulted in loss of approximately 60% of the genomic DNA of viable cells harvested in log phase[10]. It was observed in this study that EMA also readily penetrates viable cells of other bacterial species resulting in partial DNA loss. The lack of selectivity and of overall applicability led to testing a newly developed alternative chemical: Propidium monoazide (PMA). PMA is identical to PI except that the additional presence of an azide group allows crosslinkage to DNA upon light-exposure. As PI is highly membrane impermeant and generally excluded from viable cells, it has been extensively used to identify dead cells in mixed populations. Upon penetrating compromised cell membranes, PI binds to DNA by intercalating between the bases with little or no sequence preference and with a stoichiometry of one dye molecule per 4-5 base pairs of DNA[17].

The higher charge of the PMA molecule (2 positive charges compared to only one in the case of EMA) and the fact that selective staining of nonviable cells with propidium iodide (PI) has been successfully performed on a wide variety of cell types, gave confidence that the use of PMA might mitigate the drawbacks observed with EMA.

The invention examined the suitability of PMA to selectively remove detection of genomic DNA of dead cells from bacterial cultures with defined portions of live and dead cells. Because this is a newly developed molecule, optimization of the methods was necessary. Photo exposure time for DNA binding and simultaneous inactivation of free unbound PMA was optimized using purified DNA. PMA concentration and incubation time were optimized with one gram-negative and one gram-positive organism before applying these parameters to the study of a broad-spectrum of different bacterial species.

SUMMARY OF THE INVENTION

The invention comprises a method for limiting molecular diagnostics to the portion of a microbial community with intact cell membranes. This is achieved by exposing a mixture of intact and membrane-compromised cells to a phenanthridium derivative. In one embodiment said phenanthridium derivative is phenanthridium, 3-amino-8-azido-5-[3-(diethylmethylammonio)propyl]-6-phenyl dichloride. In another embodiment, said method comprises isolating genomic DNA from said mixture. In another embodiment, wherein PCR is performed using genomic DNA from the mixture as a template.

The invention also comprises a method of testing the efficacy of treatment with a disinfectant and/or antibiotic, exposing a cell culture to a candidate disinfectant and/or antibiotic; further exposing said cell culture to a phenanthridium derivative; exposing said sample with said phenanthridium derivative containing sample to a light source; isolating genomic DNA from the said sample; and performing PCR on said isolated DNA, then comparing PCR results between said disinfectant treated cultures with untreated cultures. In one embodiment said, phenanthridium derivative is PMA. In another embodiment, culture comprises an organism from the group consisting of *Salmonella enterica*, *Listeria monocytogenes*, *E. coli* and *Mycobacterium avium*. In another embodiment, said cell mixture comprises more than one organism. In another embodiment, said method can be applied to a wide range of bacterial species and any other cells where cell membrane perforation allows the uptake of the nucleic acid intercalating dye.

The invention also comprises a method of testing a disinfectant and/or antibiotic comprising, exposing a cell culture to a candidate disinfectant and/or antibiotic; further exposing said cell culture to a phenanthridium derivative; exposing said cell culture with said phenanthridium derivative containing sample to a light source; isolating RNA from said cell culture; and performing RT-PCR on isolated RNA; then comparing RT-PCR results between said disinfectant treated cultures with untreated cultures. In another embodiment, said phenanthridium derivative is PMA.

The invention also comprises a method of genotypic profiling of a sample; exposing said sample to phenanthridium derivative; exposing said phenanthridium derivative containing sample to a light source; isolating genomic DNA said sample; and performing PCR on said isolated DNA. In another embodiment, said sample is selected from the group consisting of soil, water, sewage, food, agricultural, pharmaceuticals and cosmetics (in general any sample which comprises a mixture of potentially dead and live cells). The method is believed to work with any organism for which propidium iodide and derivatives work to assess membrane integrity. This would include eukaryotic cells and fungi. In another embodiment, said phenanthridium derivative is PMA.

DESCRIPTION OF THE TEXT FILE SUBMITTED ELECTRONICALLY

Figure 1:
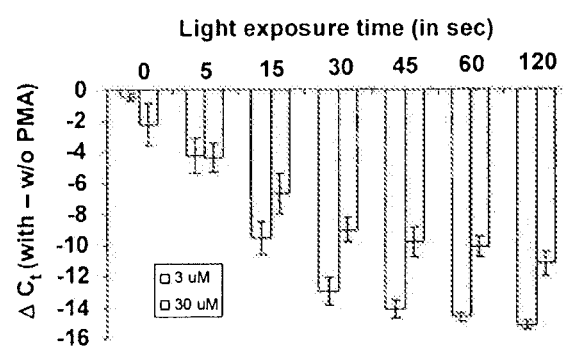
FIG. 1. Effect of increasing light exposure time on inhibition of PCR amplification by PMA. PMA was added at concentrations of 3 and 30 μM to 1 ng/μl genomic DNA extracted from *E. coli* O157:H7, followed by light exposure up to 2 minutes. Signal reduction was determined by qPCR detecting relative differences in amplifiable stx1 gene copies. $C_t$ values derived from PMA-treated samples were subtracted from the corresponding $C_t$ values from identical non-PMA treated samples. Error bars represent standard deviations from three independent replicates.

The contents of the text file submitted electronically herewith are incorporated herein by reference in their entirety: The computer readable format copy of the Sequence Listing (filename: MONT_049_01US_SeqListing_ST25.txt, date recorded, May 14, 2012, file size 4 kilobytes)

DETAILED DESCRIPTION

A new method for distinguishing between live and dead cells has been developed. It consists of a fast and easy-to perform treatment of a sample with a novel chemical (propidium monoazide, PMA) that limits diagnostic analysis to the live portion of mixed communities comprising both live and dead cells. This distinction is essential e.g. in microbial pathogen diagnostics as the potential risk from pathogens is normally limited to the live fraction of a bacterial community. The definition of live-dead distinction is based on membrane integrity, which is a well-accepted criterion for distinguishing live from dead cells: Cells with intact cell membranes are considered 'live' (as they have the potential to perform metabolic reactions or to replicate), cells with compromised membranes are considered 'dead'.

Traditionally, risk evaluation has been performed using cultivation-based approaches or plate counts. The more colonies were counted, the more pathogens were estimated to be in the original sample. Problems, however, arise from long incubation times (in the range of days) making this method unsuitable for timely warning and preventive action. Moreover, research has recently discovered that some organisms can, under certain circumstances, lose the ability to replicate although they are still viable. These 'viable but not culturable' (VBNC) bacteria cannot be detected using traditional cultivation but might regain their ability to grow if transferred to a more appropriate environment. These two drawbacks could theoretically be solved by applying molecular approaches based on the detection of genetic material/DNA of these organisms. The recent advances in molecular diagnostics enable researchers to analyze the presence or absence of target DNA within hours instead of days. These techniques can also target bacteria in the VBNC state. One of the major drawbacks, however, is the inability of DNA-based methods to discriminate between live and dead bacteria. This problem has hampered the application of these methods in many fields. Due to the persistence of DNA after cell death, DNA-based quantification can lead to a substantial overestimation of the pathogenic risk or provide false-positive results. Detection of a more labile version of genetic material, RNA, would circumvent this problem as RNA degrades rapidly after cell death, but the same instability results in technical problems if used as a molecular target. It would be optimal to combine the fast identification of bacteria using molecular techniques with the ability to distinguish between live and dead organisms. The present invention provides novel chemicals and methods for selectively excluding DNA of dead cells from a mixture containing live and dead cells from molecular detection. In other words: The present invention allows to selectively limit molecular diagnostics to the portion of mixed cells which has intact non-compromised cell membranes.

This invention provides novel phenanthridium derivatives that are highly selective in penetrating only into 'dead' bacterial cells with compromised membrane integrity but not into live cells with intact cell membranes/cell walls. The term "derivatives" as used herein refers to any compounds that are made from the phenanthridiums by reacting the phenanthridiums with one or more chemical reagents. The term also refers to any products obtainable by substituting the phenanthridium ring with different functional groups to form, for example, an azide, an acid, ester, amide, or any other products thereof. The phenanthridium derivatives can include one or more aromatic rings, typically carbocyclic aromatic ring. The aromatic ring can be a substituted or unsubstituted aryl, heteroaryl, or cycloalkyl having 3-10 carbons. As used herein, an aryl is a phenyl or a naphthyl group, and a heteroaryl substituent is a 5 or 6-membered heteroaromatic ring, wherein the heteroatom is O, N or S. The phenanthridium derivative is optionally substituted by halogen, amino, alkyl, perfluoroalkyl, alkylamino, dialkylamino, alkoxy or carboxyalkyl, wherein each alkyl group has 1-6 carbons. The phenanthridium derivative is preferably substituted by an azide group, a substituted or unsubstituted phenyl, phenylnaphthyl, or cycloalkyl having 3-10 carbons. More preferably, the phenanthridium derivative comprises one or more azide moieties and is substituted at 6 position with a phenyl. Illustrative examples of useful phenanthridium derivatives are propidium monoazide (PMA) and ethidium monoazide (EMA). More preferably, the compound is phenanthridium, 3-amino-8-azido-5-[3-(diethylmethylammonio)propyl]-6-phenyl dichloride. One important feature of the compounds utilized in the present invention is that it can modify nucleic acids like DNA. The nature of this modification is believed to be covalent crosslinkage, but it could also be of any other nature which interferes with the PCR amplification of such modified nucleic acids. This modification has the potential also to interfere with other enzymatic processes in which DNA (or RNA) is involved.

Thus one embodiment of the invention comprises a method of distinguishing dead cells from live cells comprising exposing a mixture of live and dead cells to phenanthridium derivative of formula (I):

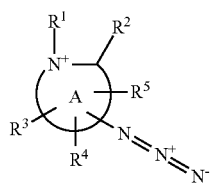

(I)

wherein
ring A is a fused polycyclic ring comprising at least one aryl ring and at least one heteroaryl ring;
$R^1$ is alkyl having 1 to 6 carbon atoms, perfluoroalkyl having 1 to 6 carbon atoms, or tetra-alkyl ammonium;
$R^2$ is a substituted or unsubstituted aryl, substituted or unsubstituted heteroaryl, or substituted or unsubstituted cycloalkyl having 3 to 10 carbon atoms;
$R^3$ is amino, N-alkylamino, N,N-dialkylamino, alkoxy, or carboxyalkyl; and
$R^4$ and $R^5$ are independently selected from the group consisting of hydrogen, halide, hydroxyl, amino, N-alkylamino, N,N-dialkylamino, alkoxy, carboxyalkyl, alkyl having 1 to 6 carbon atoms, perfluoroalkyl having 1 to 6 carbon atoms, azide, and tetra-alkyl ammonium;
or a mono or bis halide salt thereof.

In another embodiment, said phenanthridium derivative has a structure of formula (II):

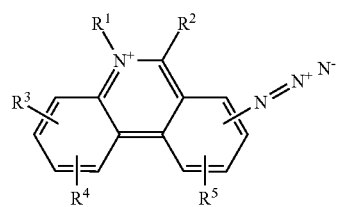

(II)

wherein
$R^1$ is alkyl having 1 to 6 carbon atoms, perfluoroalkyl having 1 to 6 carbon atoms, or tetra-alkyl ammonium;
$R^2$ is a substituted or unsubstituted aryl, substituted or unsubstituted heteroaryl, or substituted or unsubstituted cycloalkyl having 3 to 10 carbon atoms;
$R^3$ is amino, N-alkylamino, N,N-dialkylamino, alkoxy, or carboxyalkyl; and
$R^4$ and $R^5$ are independently selected from the group consisting of hydrogen, halide, hydroxyl, amino, N-alkylamino, N,N-dialkylamino, alkoxy, carboxyalkyl, alkyl having 1 to 6 carbon atoms, perfluoroalkyl having 1 to 6 carbon atoms, azide, and tetra-alkyl ammonium;
or a mono or bis halide salt thereof.

In another embodiment, said phenanthridium derivative has a structure of formula (III):

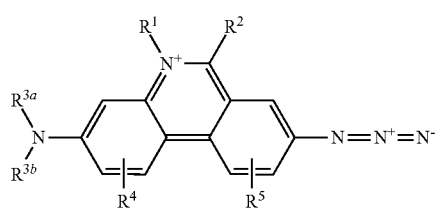

(III)

wherein
$R^1$ is alkyl having 1 to 6 carbon atoms, perfluoroalkyl having 1 to 6 carbon atoms, or tetra-alkyl ammonium;
$R^2$ is a substituted or unsubstituted aryl, substituted or unsubstituted heteroaryl, or substituted or unsubstituted cycloalkyl having 3 to 10 carbon atoms;
$R^{3a}$ and $R^{3b}$ are independently hydrogen or alkyl having 1 to 6 carbon atoms; and
$R^4$ and $R^5$ are independently selected from the group consisting of hydrogen, halide, hydroxyl, amino, N-alkylamino, N,N-dialkylamino, alkoxy, carboxyalkyl, alkyl having 1 to 6 carbon atoms, perfluoroalkyl having 1 to 6 carbon atoms, azide, and tetra-alkyl ammonium;
or a mono or bis halide salt thereof.

In another embodiment said phenanthridium derivative is selected from the group consisting of 3-amino-8-azido-5-ethyl-6-phenylphenanthridinium iodide, 3-amino-8-azido-5-ethyl-6-phenylphenanthridinium bromide, 3-amino-8-azido-5-ethyl-6-phenylphenanthridinium chloride, 3-amino-8-azido-5-(3-(diethylmethylammonio)propyl)-6-phenylphenanthridium diiodide, 3-amino-8-azido-5-(3-(diethylmethylammonio)propyl)-6-phenylphenanthridium dibromide, and 3-amino-8-azido-5-(3-(diethylmethylammonio)propyl)-6-phenylphenanthridium dichloride. In another embodiment, the phenanthridium derivative is PMA (propidium monoazide) as represented by formula IV:

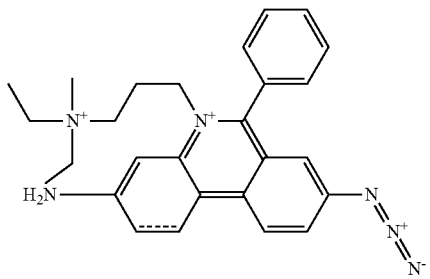

The derivatives also include dimers and multimers of the stated chemicals or molecules with modified electrical charges. Said modification electrical charges can be accomplished with counterions. The counterions can be any atom that can form an anion, e.g. iodide, bromide, chloride.

In another embodiment, said method comprises isolating genomic DNA from said mixture. In another embodiment, PCR is performed to said mixture. In another embodiment, said method comprises isolating RNA from said mixture. In another embodiment, RT-PCR is performed to said isolated RNA.

Upon intercalation in the DNA of dead cells, the photo-inducible azide group allows PMA to be covalently cross-linked by exposure to bright light. This process may render the DNA insoluble and results in its loss during subsequent genomic DNA extraction or PMA treatment may results in a modification of the DNA from cells with compromised membranes that results in inhibition of its PCR amplification. Subjecting a cell population comprised of both live and dead cells to PMA treatment thus results in undetectable DNA from dead cells. This invention provides evidence that the method can be applied to a wide range of species across the bacterial kingdom presenting a major advantage over ethidium monoazide (EMA). Although the same general principle has recently been shown to work with EMA, its overall application is hampered by the fact that the chemical can also penetrate live cells of some bacterial species. Despite transport pumps actively exporting EMA out of metabolically active cells, the remaining EMA level can lead to substantial loss of DNA from these cells. The higher charge of PMA might be the reason for the higher impermeability through intact cell membranes, thus avoiding DNA loss.

The present invention has applications in any and all methods, procedures and processes involving DNA diagnostics. Examples of such applications include but are not limited to those involving food, water safety, bioterrorism, medical/medicines and/or anything involving pathogen detection. This invention also provides methods of using PMA to monitor the disinfection efficacy of model pathogens using chlorine and has major applications in the water industry. In the food industry, the present invention can be used to monitor the efficacy of preservatives. The method can be applied to all cell types as long as an intact membrane excludes the phenanthridium derivative from entering the cell and as long as the phenanthridium derivative can enter cells with compromised cell membranes. As propidium iodide has been shown to work with animal, fungal and parasitic cells, the method of the invention has the potential to be applied to all cells. Although bacterial cells are exemplified in the examples, the methods of the invention to be applied to other cell types.

The invention can also be used for the identification of substances that can disrupt membranes and/or kill cells, e.g. bacterial cells. The identification of new disinfectants and/or antibiotics are now a priority since multidrug resistance organisms have flourished and spread in health institutions and patients. Thus, the invention encompasses a method of testing a disinfectant and/or antibiotic comprising,
 a. exposing a cell culture to a candidate disinfectant and/or antibiotic;
 b. further exposing said cell culture to a phenanthridium derivative;
 c. exposing said sample with said phenanthridium derivative containing sample to a light source;
 d. isolating genomic DNA said sample; and
 e. performing PCR on said isolated DNA;
then comparing PCR results between said disinfectant treated cultures with untreated cultures. In one embodiment, said cell culture is a bacterial cell culture, fungal cell culture or animal cell culture. In another embodiment, said phenanthridium derivative is PMA. The concentration PMA can be adjusted according to the nature of the sample (depending on the number of cells, the cell type, the membrane characteristics of the cells, the purity, the permeability of the sample for the chemical, etc.). The incubation time can be adjusted according to the nature of the sample (depending on the number of cells, the cell type, the membrane characteristics of the cells, the purity, the permeability of the sample for the chemical, etc.). In one embodiment, approximately 20 µM to about 240 µM of PMA is added to the said cell culture. In another embodiment, approximately 50 µM of PMA is added to said cell culture. In another embodiment, said cell culture is exposed to PMA for about 1.0 to about 60 minutes. In another embodiment, said cell culture is exposed to PMA for about 5 minutes (or for some different time period depending on the nature of the sample). Any light source used should comprise the wavelengths that are necessary for the activation of the chemical. In another embodiment, said light source is a 650 watt halogen lamp. In another embodiment, the distance of the said light source is in the range from minimal distance to 100 cm from said cell culture. In another embodiment, said cell culture can comprise a pathogen. In another embodiment, said cell culture comprises an organism from the group consisting of *Salmonella enterica, Listeria monocytogenes, E. coli, Campylobacter jejuni,* and *Mycobacterium avium*. In another embodiment, said culture comprises more than one organism. In another embodiment, said disinfectant and/or antibiotics compromises membrane integrity.

The method, in combination with quantitative PCR as a tool, can quickly and successfully identify the impact of a disinfectant and/or antibiotic without having to spend time culturing the cells and waiting for growth. In some instances, organisms can take days to weeks to culture, and thus it can take significant time to see if the candidate substance has been able to kill cells, like microorganisms. In other instances, certain organisms will not grow in cell culture, therefore making it difficult to determine if a substance was effective. Thus, applying methods of the invention saves time and resources for identification of novel disinfectants and/or antibiotics. The method of the invention has successfully monitored the disinfection efficacy of hypochlorite, benzalkonium and heat on several model pathogens (see below). In addition to modifying DNA, the PMA has been shown to modify RNA. Thus, one embodiment of the invention comprises a method of testing a disinfectant comprising,
 a. exposing a cell culture to a candidate disinfectant and/or antibiotic;

b. further exposing said cell culture to a phenanthridium derivative;
c. exposing said sample with said phenanthridium derivative containing sample to a light source;
d. isolating RNA from cell culture; and
e. performing RT-PCR on isolated RNA;

then comparing RT-PCR results between said disinfectant treated cultures with untreated cultures. In one embodiment said cell culture is a bacterial cell culture, fungal cell culture or animal cell culture. In another embodiment, wherein said phenanthridium derivative is PMA.

The concentration of PMA can be adjusted according to the nature of the sample (depending on the number of cells, the cell type, the membrane characteristics of the cells, the purity, the permeability of the sample for the chemical, etc.). In one embodiment, approximately 20 µM to about 240 µM of PMA is added to the said cell culture. In another embodiment, approximately 50 µM of PMA is added to said cell culture. The incubation time can be adjusted according to the nature of the cell culture (depending on the number of cells, the cell type, the membrane characteristics of the cells, the purity, the permeability of the sample for the chemical, etc.). In one embodiment, said cell culture is exposed to PMA for about 1.0 to about 60 minutes. In another embodiment, said cell culture is exposed to PMA for about 5 minutes (or for some different time period depending on the nature of the sample). Any light source used should comprise the wavelengths that are necessary for the activation of the chemical. In one embodiment, said light source is a 650 watt halogen lamp. In another embodiment, the distance of the said light source is in the range from minimal distance to 100 cm from the said sample. In another embodiment, said culture comprises an organism from the group consisting of *Salmonella enterica, Listeria monocytogenes, E. coli, Campylobacter jejuni*, and *Mycobacterium avium*. In another embodiment, said culture comprises more than one organism. In another embodiment, said disinfectant disrupts membrane integrity. The method, in combination with RT-PCR as a tool, can quickly and successfully identify a disinfectant and/or antibiotic without having to spend time culturing the cells and waiting for growth.

An advantage of the methods according to the invention is the ease of use. For example, using these methods, large amounts of samples can easily be tested for the presence of viable cells, e.g. bacteria. The methods according to the invention may be used in various ways. For example, food samples (e.g., poultry, fresh meat, milk, cheese, vegetables, fruit, fish, etc.) may be tested for the presence of potentially live bacteria with intact cell membranes. In another embodiment, environmental samples may be tested for the presence of viable cells, e.g. bacteria.

These samples may be, for example, collected from soil or be parts of plants. The method according to the invention may further be used for testing of treated waste water before and after release.

The method according to the invention may further be used for testing medicinal samples, e.g., stool samples, blood cultures, sputum, tissue samples (also cuts), wound material, urine, samples from the respiratory tract, implants and catheter surfaces.

Another field of application of the method according to the invention is the control of foodstuffs. In other embodiments, the food samples are obtained from milk or milk products (yogurt, cheese, sweet cheese, butter, and buttermilk), drinking water, beverages (lemonades, beer, and juices), bakery products or meat products. The method of the invention can determine if preservatives in the food or antimicrobial treatment of food (such as pasteurization) has prevented cell growth. A further field of application of the method according to the invention is the analysis of pharmaceutical and cosmetic products, e.g. ointments, creams, tinctures, juices, solutions, drops, etc.

Thus, in another embodiment, the invention comprises a method of microbial profiling a sample comprising,
a. collecting a sample;
b. exposing said sample to phenanthridium derivative;
c. exposing said phenanthridium derivative containing sample to a light source;
d. isolating genomic DNA said sample; and
e. performing PCR on said isolated DNA.

In another embodiment, said sample is selected from the group consisting of soil, water, sewage, food, agricultural, pharmaceuticals and cosmetics. In another embodiment, wherein said phenanthridium derivative is PMA. The concentration of PMA can be adjusted according to the nature of the sample (depending on the number of cells, the cell type, the membrane characteristics of the cells, the purity, the permeability of the sample for the chemical, etc.). In one embodiment, approximately 20 µM to about 240 µM of PMA is added to the said sample. In another embodiment, approximately 50 µM of PMA is added to said sample. The incubation time can be adjusted according to the nature of the sample (depending on the number of cells, the cell type, the membrane characteristics of the cells, the purity, the permeability of the sample for the chemical, etc.). In one embodiment, said sample is exposed to PMA for about 1.0 to about 60 minutes. In another embodiment, said sample is exposed to PMA for about 5 minutes (or for some different time period depending on the nature of the sample). Any light source used should comprise the wavelengths that are necessary for the activation of the chemical. In one embodiment, said light source is a 650 watt halogen lamp. In another embodiment, the distance of the said light source is in the range from minimal distance to 100 cm from the said sample. In another embodiment, said sample comprises an organism from the group consisting of *Salmonella enterica, Listeria monocytogenes, E. coli, Campylobacter jejuni*, and *Mycobacterium avium*. In another embodiment, said sample comprises more than one organism. The method can be used for a rapid detection of viable organisms in soil, water, sewage, food, agricultural, pharmaceuticals and cosmetics.

The method of the invention solves the problem of long incubation times (in the range of days) making the older methods unsuitable for timely warning and preventive action. In addition, modern PCR based methods can give a false positives (testing positive for an organism although the organism is not viable). Moreover, research has recently discovered that some organisms can, under certain circumstances, lose the ability to replicate although they are still viable. These 'viable but not culturable' (VBNC) bacteria cannot be detected using traditional cultivation but might regain their ability to grow if transferred to a more appropriate environment. These drawbacks are solved by applying molecular approaches based on the detection of genetic material/DNA of these organisms in combination with the methods of the invention. Thus, quick and accurate results regarding viable organisms is a sample, e.g. contaminated water, sewage, food, pharmaceuticals and/or cosmetics, can prevent contaminated products from being released to the public. The methods of the invention can save resources, by minimizing false positives (testing positive for a pathogen although the pathogen is not viable) and rapid testing of samples, as compared to the current time consuming methods.

In addition, the method of the invention can identify potentially viable members of a microbial community for ecological studies, health of specific soils for agricultural and/or ecological systems. Traditionally identifying a bacterial community has been performed using cultivation-based approaches or plate counts. The more colonies were counted, the more bacteria are estimated to be in the original sample. Problems, however, arise from sometimes long incubation times (in the range of days) making this method unsuitable for timely and accurate results. These drawbacks are solved by applying molecular approaches based on the detection of genetic material/DNA of these organisms with the methods of the invention.

In another embodiment, the invention comprises a method of microbial profiling of a sample comprising,
a. collecting a sample;
b. exposing said sample to phenanthridium derivative;
c. exposing said phenanthridium derivative containing sample to a light source;
d. isolating RNA from said sample; and
e. performing RT-PCR on said isolated RNA.

In another embodiment, said sample is selected from the group consisting of soil, water, sewage, food, agricultural, pharmaceuticals and cosmetics. In another embodiment, wherein said phenanthridium derivative is PMA. In another embodiment, approximately 20 μM to about 240 μM of PMA is added to the said sample. In another embodiment, approximately 50 μM of PMA is added to said sample. In another embodiment, said sample is exposed to PMA for about 1.0 to about 20 minutes. In another embodiment, said sample is exposed to PMA for about 5 minutes. In another embodiment, said light source is a 650 watt halogen lamp. In another embodiment, said light source is about 1.0 to about 100 cm from said sample. In another embodiment, said culture comprises an organism from the group consisting of *Salmonella enterica, Listeria monocytogenes, E. coli, Campylobacter jejuni*, and *Mycobacterium avium*.

Non-limiting examples of bacteria can be used to test candidate disinfectants and/or antibiotics and/or to detect potential viability in a sample using the method of the invention comprises: *B. pertussis, Leptospira pomona, S. paratyphi* A and B, *C. diphtheriae, C. tetani, C. botulinum, C. perfringens, C. feseri* and other gas gangrene bacteria, *B. anthracis, P. pestis, P. multocida, Neisseria meningitidis, N. gonorrheae, Hemophilus influenzae, Actinomyces* (e.g., *Norcardia*), *Acinetobacter, Bacillaceae* (e.g., *Bacillus anthrasis*), *Bacteroides* (e.g., *Bacteroides fragilis*), Blastomycosis, *Bordetella, Borrelia* (e.g., *Borrelia burgdolferi*), *Brucella, Campylobacter, Chlamydia, Coccidioides, Corynebacterium* (e.g., *Corynebacterium diptheriae*), *E. coli* (e.g., Enterotoxigenic *E. coli* and Enterohemorrhagic *E. coli*), *Enterobacter* (e.g. *Enterobacter aerogenes*), Enterobacteriaceae (*Klebsiella, Salmonella* (e.g., *Salmonella typhi, Salmonella enteritidis, Serratia, Yersinia, Shigella*), *Erysipelothrix, Haemophilus* (e.g., *Haemophilus influenza* type B), *Helicobacter, Legionella Legionella pneumophila*), *Leptospira, Listeria* (e.g., *Listeria monocytogenes*), *Mycoplasma, Mycobacterium* (e.g., *Mycobacterium leprae* and *Mycobacterium tuberculosis*), *Vibrio* (e.g., *Vibrio cholerae*), Pasteurellacea, *Proteus, Pseudomonas* (e.g., *Pseudomonas aeruginosa*), Rickettsiaceae, *Spirochetes* (e.g., *Treponema* spp., *Leptospira* spp., *Borrelia* spp.), *Shigella* spp., *Meningiococcus, Pneumococcus* and *Streptococcus* (e.g., *Streptococcus pneumoniae* and Groups A, B, and C Streptococci), Ureaplasmas. *Treponema pollidum, Staphylococcus aureus, Pasteurella haemolytica, Corynebacterium diptheriae* toxoid, Meningococcal polysaccharide, *Bordetella pertusis, Streptococcus pneumoniae, Clostridium tetani* toxoid, and *Mycobacterium Bovis*. The above list are meant to be illustrative and by no means are meant to limit the invention to detection to those particular bacterial organisms.

One embodiment for detecting microorganisms is via PCR. General procedures for PCR are taught in U.S. Pat. No. 4,683,195 (Mullis et al.) and U.S. Pat. No. 4,683,202 (Mullis et al.). However, optimal PCR conditions used for each amplification reaction are generally empirically determined or estimated with computer software commonly employed by artisans in the field. A number of parameters influence the success of a reaction. Among them are annealing temperature and time, extension time, $Mg^{2+}$, pH, and the relative concentration of primers, templates, and deoxyribonucleotides. Generally, the template nucleic acid is denatured by heating to at least about 95° C. for 1 to 10 minutes prior to the polymerase reaction. Approximately 20-99 cycles of amplification are executed using denaturation at a range of 90° C. to 96° C. for 0.05 to 1 minute, annealing at a temperature ranging from 48° C. to 72° C. for 0.05 to 2 minutes, and extension at 68° C. to 75° C. for at least 0.1 minute with an optimal final cycle. In one embodiment, a PCR reaction may contain about 100 ng template nucleic acid, 20 uM of upstream and downstream primers, and 0.05 to 0.5 mm dNTP of each kind, and 0.5 to 5 units of commercially available thermal stable DNA polymerases.

A variation of the conventional PCR is reverse transcription PCR reaction (RT-PCR), in which a reverse transcriptase first coverts RNA molecules to single stranded cDNA molecules, which are then employed as the template for subsequent amplification in the polymerase chain reaction. Isolation of RNA is well known in the art. In carrying out RT-PCR, the reverse transcriptase is generally added to the reaction sample after the target nucleic acid is heat denatured. The reaction is then maintained at a suitable temperature (e.g. 30-45° C.) for a sufficient amount of time (10-60 minutes) to generate the cDNA template before the scheduled cycles of amplification take place. One of skill in the art will appreciate that if a quantitative result is desired, caution must be taken to use a method that maintains or controls for the relative copies of the amplified nucleic acid. Methods of "quantitative" amplification are well known to those of skill in the art. For example, quantitative PCR can involve simultaneously co-amplifying a known quantity of a control sequence using the same primers. This provides an internal standard that may be used to calibrate the PCR reaction.

Another alternative of PCR is quantitative PCR (qPCR). qPCR can be run by competitive techniques employing an internal homologous control that differs in size from the target by a small insertion or deletion. However, non-competitive and kinetic quantitative PCR may also be used. Combination of real-time, kinetic PCR detection together with an internal homologous control that can be simultaneously detected alongside the target sequences.

Primers for PCR, RT-PCR and/or qPCR are selected within regions or specific bacteria which will only amplify a DNA region which is selected for that specific organism. Alternatively, primers are selected which will hybridize and amplify a section of DNA which is common for all organisms. Primer selection and construction is generally known in the art. In general, one primer is located at each end of the sequence to be amplified. Such primers will normally be between 10 to 35 nucleotides in length and have a preferred length from between 18 to 22 nucleotides. The smallest sequence that can be amplified is approximately 50 nucleotides in length (e.g., a forward and reverse primer, both of 20 nucleotides in length, whose location in the sequences is separated by at least 10 nucleotides). Much longer sequences can be amplified. One primer is called the "forward primer" and is located at the left end of the region to be amplified. The forward primer is identical in sequence to a region in the top strand of the DNA (when a double-stranded DNA is pictured using the convention where the top strand is shown with polarity in the 5' to 3' direction). The sequence of the forward primer is such that it hybridizes to the strand of the DNA which is complementary to the top strand of DNA. The other primer is called the "reverse primer" and is located at the right end of the region to be amplified. The sequence of the reverse primer is such that it is complementary in sequence to, i.e., it is the reverse complement of a sequence in, a region in the top strand of the DNA. The reverse primer hybridizes to the top end of the DNA.

PCR primers should also be chosen subject to a number of other conditions. PCR primers should be long enough (preferably 10 to 30 nucleotides in length) to minimize hybridization to greater than one region in the template. Primers with long runs of a single base should be avoided, if possible. Primers should preferably have a percent G+C content of between 40 and 60%. If possible, the percent G+C content of the 3' end of the primer should be higher than the percent G+C content of the 5' end of the primer. Primers should not contain sequences that can hybridize to another sequence within the primer (i.e., palindromes). Two primers used in the same PCR reaction should not be able to hybridize to one another. Although PCR primers are preferably chosen subject to the recommendations above, it is not necessary that the primers conform to these conditions. Other primers may work, but have a lower chance of yielding good results.

PCR primers that can be used to amplify DNA within a given sequence can be chosen using one of a number of computer programs that are available. Such programs choose primers that are optimum for amplification of a given sequence (i.e., such programs choose primers subject to the conditions stated above, plus other conditions that may maximize the functionality of PCR primers). One computer program is the Genetics Computer Group (GCG recently became Accelrys) analysis package which has a routine for selection of PCR primers.

The oligonucleotide primers and probes disclosed below can be made in a number of ways. One way to make these oligonucleotides is to synthesize them using a commercially-available nucleic acid synthesizer. A variety of such synthesizers exists and is well known to those skilled in the art.

Another alternative of PCR is isothermal nucleic acid amplification assay for the detection of specific DNA or RNA targets. Non-limiting examples for isothermal amplification of nucleic acids are homogeneous real-time strand displacement amplification, Phi29 DNA polymerase based rolling circle amplification of templates for DNA sequencing, rolling-circle amplification of duplex DNA sequences assisted by PNA openers or loop-mediated isothermal amplification of DNA analytes.

Nucleic acid may also be detected by hybridization methods. In these methods, labeled nucleic acid may be added to a substrate containing labeled or unlabeled nucleic acid probes. Alternatively, unlabeled or unlabeled nucleic acid may be added to a substrate containing labeled nucleic acid probes. Hybridization methods are disclosed in, for example, MicroArray Analysis, Marc Schena, John Wiley and Sons, Hoboken N.J. 2003.

Methods of detecting nucleic acids can include the use of a label. For example, radiolabels may be detected using photographic film or a phosphoimager (for detecting and quantifying radioactive phosphate incorporation). Fluorescent markers may be detected and quantified using a photodetector to detect emitted light (see U.S. Pat. No. 5,143,854, for an exemplary apparatus). Enzymatic labels are typically detected by providing the enzyme with a substrate and measuring the reaction product produced by the action of the enzyme on the substrate. Colorimetric labels are detected by simply visualizing the colored label.

In one embodiment, the amplified nucleic acid molecules are visualized by directly staining the amplified products with a nucleic acid-intercalating dye. As is apparent to one skilled in the art, exemplary dyes include but not limited to SYBR green, SYBR blue, DAPI, propidium iodine, Hoeste, SYBR gold and ethidium bromide. The amount of luminescent dyes intercalated into the amplified DNA molecules is directly proportional to the amount of the amplified products, which can be conveniently quantified using a FluoroImager (Molecular Dynamics) or other equivalent devices according to manufacturers' instructions. A variation of such an approach is gel electrophoresis of amplified products followed by staining and visualization of the selected intercalating dye. Alternatively, labeled oligonucleotide hybridization probes (e.g. fluorescent probes such as fluorescent resonance energy transfer (FRET) probes and colorimetric probes) may be used to detect amplification. Where desired, a specific amplification of the genome sequences representative of the biological entity being tested, may be verified by sequencing or demonstrating that the amplified products have the predicted size, exhibit the predicted restriction digestion pattern, or hybridize to the correct cloned nucleotide sequences.

The invention also comprises kits. For example, the kit can comprise primers useful for amplifying nucleic acid molecule corresponding to organisms specifically or generally, a phenanthridium derivative (e.g. PMA), buffers and reagents for isolating DNA, and reagents for PCR. The kit can also include detectably labeled oligonucleotide, which hybridizes to a nucleic acid sequence encoding a polypeptide corresponding to organisms of interest. The kit can also contain a control sample or a series of control samples which can be assayed and compared to a test sample contained. Each component of the kit can be enclosed within an individual container and all of the various containers can be within a single package, along with instructions for interpreting the results of the assays performed using the kit.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Material and Methods

Bacterial Strains and Culture Conditions.

The bacterial strains used for this study comprise 4 gram-negative and 5 gram-positive species and are listed together with the corresponding media and growth temperatures in Table 1. Single colonies from agar streak plates were typically transferred to 50 ml culture tubes containing about 10 ml of the corresponding medium. The cultures were grown to log phase in a shaker at 180 rpm at the given growth temperature. For experiments involving quantitative qPCR, optical densities of E. coli 0157:H7 cultures were adjusted to an $OD_{600}$ of 1 by dilution with LB broth.

Killing Conditions.

Figure 4:
FIG. 4. Effect of PMA treatment on genomic DNA yield and PCR-quantification of defined ratios of viable and heat-killed cells. The error bars represent standard deviations from three independent replicates. (A) Table showing mixing ratios of viable and heat-killed *E. coli* O157:H7. Numbers represent volumes in (B) Genomic DNA from non-PMA treated (top) and PMA-treated (bottom) mixtures visualized on an agarose gel. (C) Genomic DNA yield in percent of the highest value obtained. DNA was quantified using a fluorometer. (D) $C_t$ values of amplified genomic DNA shown as a function of the percentage of viable cells. qPCR was performed using primers specific for the stx1 gene. (E) Correlation between the natural logarithm of the normalized DNA concentrations and the corresponding $C_t$ values obtained from stx1 amplification. The $R^2$ value of the linear trendline is indicated.
Figure 4:
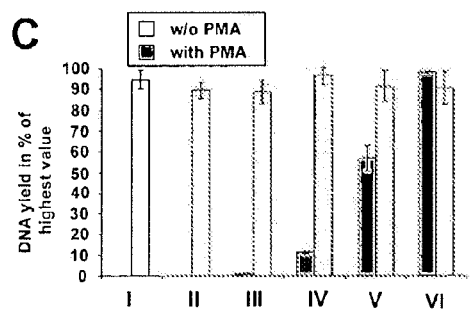
Figure 4:
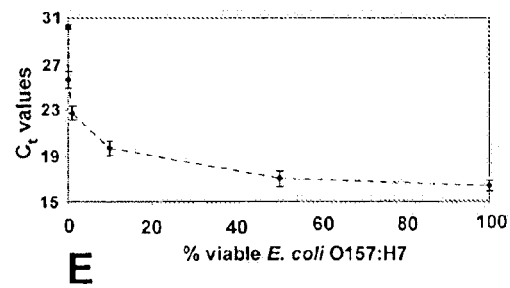
Figure 4:
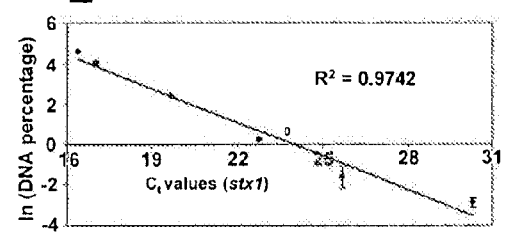

Cells in 500 µl aliquots were killed by exposure to isopropanol (final concentration 70%) for 10 minutes. Isopropanol was removed by harvesting cells using centrifugation at 5000 g for 5 minutes prior to resuspension in 500 µl of the corresponding medium. As an alternative to isopropanol treatment, *Mycobacterium avium* and *Micrococcus luteus* cells were killed by heating for 15 minutes to 85° C. and 72° C., respectively. To study the effect of PMA on defined ratios of viable and dead cells (FIG. 4) *E. coli* O157:H7 was heat-killed by exposure to 72° C. for 15 minutes prior to mixing at defined ratios with untreated cells. Loss of viability was examined by streaking 5 µl of cell suspension on the corresponding agar plates followed by incubation at the optimal growth temperature.

PMA and EMA Cross-Linking.

PMA (phenanthridium, 3-amino-8-azido-5-[3-(diethylmethylammonio)propyl]-6-phenyl dichloride; Biotium, Inc., Hayward, Calif.) and EMA (phenanthridium, 3-amino-8-azido-5-ethyl-6-phenyl bromide; Biotium, Inc., Hayward, Calif.) were dissolved in 20% DMSO to create a stock concentration of 20 mM or dilutions of that and stored at −20° C. in the dark. PMA was added to 500 µl culture aliquots to final concentrations of 3, 30, 50 or 240 µM. The DMSO content of PMA dilutions was chosen in a way that the final DMSO concentrations were identical for the exposed cells. Following an incubation period from 1 to 15 minutes in the dark with occasional mixing, samples were light-exposed for 5 sec to 2 minutes using a 650-W halogen light source placed 20 cm from the sample tubes. During exposure, samples were placed on ice to avoid excessive heating. After photo-induced cross-linking, cells were pelleted at 5000 g for 5 minutes prior to DNA isolation. After optimization experiments were completed, PMA was added to a final concentration of 50 µM and incubated for 5 minutes prior to light exposure for 2 minutes. The same concentration (50 µM) and procedure was applied to experiments using EMA to make results comparable with the PMA experiments.

DNA Isolation and Quantification.

Genomic DNA was extracted using the Qbiogene soil kit (Qbiogene, Carlsbad, Calif., USA) following the manufacturer's instructions. Cell lysis of pure cultures was achieved by bead beating using a FastPrep machine (Qbiogene) for 25 sec at a speed setting of 4.5 m/s. DNA was quantified using the PicoGreen quantification solution (Molecular Probes Inc., Eugene, Oreg., USA) and a TBS-380 fluorometer (Turner BioSystems Inc., Sunnyvale, Calif., USA) using genomic DNA from *E. coli* O157:H7 as a standard (with a mid-range GC content). The quantification results obtained with the fluorometer were compared with band intensities of high molecular weight genomic DNA visualized on ethidium bromide stained 1 agarose gels. Seven to ten percent of the total corresponding eluate volumes were loaded on the gels.

Quantitative PCR.

For relative quantification of DNA extracted from *E. coli* O157:1-17 cultures, the stx1 gene coding for the Shiga-like toxin 1 was used as a genetic target. qPCR was performed in a total volume of 25 µl containing 1 µl extracted genomic DNA and final concentrations of 1× AmpliTaq GOLD buffer (Applied Biosystems, Foster City, Calif., USA), 5.5 mM MgCl2, 0.3 µM of primer stx1-forward (5'-GACTGCAAA-GACGTATGTAGATTCG-3'; 16, SEQ ID NO 1), 0.3 µM of primer stx1-reverse (5'-ATCTATCCCTCTGACAT-CAACTGC-3'; 16, SEQ ID NO 2), 0.15 µM of the stx1-probe (5'-TGAATGTCATTCGCTCTG CAATAGGTACTC-3'; 16, SEQ ID NO 3) and 2.5 U of AmpliTaq Gold (Applied Biosystems). The stx1-probe had 6-FAM as the 5'-reporter and BHQ1 as the 3'-quencher. The cycling parameters were: 8 minutes at 95° C. followed by 45 cycles of 20 sec at 95° C., 30 sec at 55° C. and 25 sec at 72° C.

qPCR and data analysis were performed with a SmartCycler II (Cepheid, Sunnyvale, Calif.). Cycle threshold ($C_t$) values were automatically calculated by the SmartCycler software using the second derivative method.

Statistical Analysis.

Error bars in diagrams represent standard deviations from three independent replicas.

Fluorescence microscopy. Cells were stained for microscopy by adding 1.25 µl of the dye SYTO9 (3.34 mM in DMSO; Molecular Probes) in combination with 1.25 µl of either PMA or EMA (both 20 mM in 20% DMSO; Biotium Inc.) to 500 µl culture aliquots. SYTO9 generally stains all bacteria in a population green, while PMA and EMA stains them red if the dyes can penetrate the cell walls/membranes. After mixing, samples were mounted on microscope slides. Five minutes after addition of the dyes, photomicrographs were taken on a Nikon E800 microscope using a 100×1.4 NA oil objective and FITC and TRITC fluorescence filter sets (ex480/30, DM505, em535/40 and ex546/10, DM575, em590, respectively). The software used for visualization was MetaVue version 6.1 (Universal Imaging, Downington, Pa., USA).

Example 2

Optimization of PMA/DNA Cross-Linking Using Pure DNA

PMA was added to a solution of genomic DNA extracted from *E. coli* O157:H7 followed by light exposure for increasing time periods ranging from 0 sec to 120 sec. 1.0 µl of the 1.0 ng/µl DNA solution was used as template for quantitative PCR (qPCR) using primers and a probe targeting the stx1 gene. Increasing light exposure time led to higher threshold cycles ($C_t$ values), meaning more cycles were necessary for detecting a signal above the background. This increase in $C_t$ values indicated increasing inhibition of PCR amplification. FIG. 1 illustrates the signal reduction of PMA-treated DNA as a function of light-exposure time compared to the amplification of non-treated DNA. The strongest increase in signal reduction was observed up to 30 sec of light exposure with the inhibition curve flattening off with longer exposure times. Identical tendencies were observed for PMA concentrations of both 3 and 30 µM. The fact that 3 µM PMA led to greater inhibition of PCR amplification than 30 µM PMA was solely dependent on the $Mg^{2+}$ concentration. Different $Mg^{2+}$ concentrations had a great impact on $C_t$ values for this particular PCR reaction (data not shown). PMA concentrations of 60 µM and higher resulted in complete inhibition of the PCR reaction independent of the light exposure time (data not shown).

Figure 2:
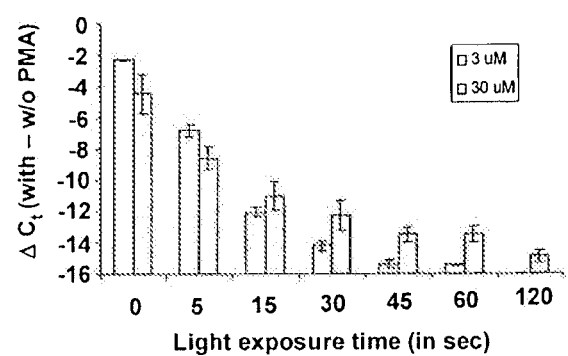
FIG. 2. Effect of increasing light exposure time on PMA inactivation. PMA at concentrations of 3 and 30 μM was light exposed up to 2 minutes before addition of genomic *E. coli* O157:H7 DNA (final concentration 1 ng/μl). After mixing, cross-linkage of remaining active PMA to DNA was achieved with an additional light exposure of 1 minutes. Signal reduction was determined by qPCR detecting relative differences in amplifiable stx1 gene copies. $C_t$ values derived from PMA-treated samples were subtracted from the corresponding $C_t$ values from identical non-PMA treated samples. Error bars represent standard deviations from three independent replicates.

The efficiency of photolysis (i.e. the inactivation of free PMA not bound to DNA) was examined by light exposing PMA solutions of 3 and 30 µM for increasing time periods prior to addition of DNA. After addition of DNA, the mixture was light exposed for another minute to achieve cross-linking of remaining active PMA to the DNA followed by qPCR. Increasing inactivation times of free PMA resulted in decreasing signal reduction relative to the identical samples without PMA (FIG. 2). In the case of 3 µM, an inactivation period of 120 sec diminished the difference between the PMA and the non-PMA containing samples.

Considering the above results, a 120 sec light exposure time was chosen to guarantee maximal binding of PMA to DNA and at the same time to achieve maximal inactivation of free PMA that did not bind to DNA. The latter is important when treating cells with PMA to make sure that no active PMA remains in solution, which could bind to DNA originating from viable cells after the cell lysis step.

Example 3

Optimization of the PMA Assay Using Cells

Figure 3:
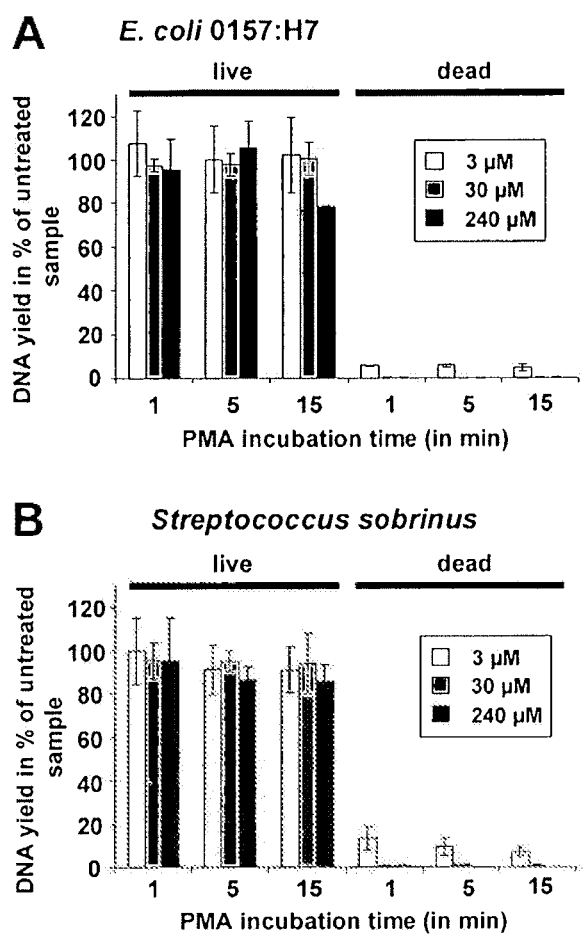
FIG. 3. Effect of increasing PMA incubation times and different PMA concentrations on the genomic DNA yield of live and isopropanol-killed *E. coli* O157:H7 (A) and *Streptococcus sobrinus* (B). Cells were exposed to PMA at concentrations of 3, 30 and 240 μM for 1, 5 or 15 minutes. The genomic DNA yield was expressed as a percentage of the corresponding non-PMA treated samples (live or dead). Error bars represent standard deviations from three independent replicates.

*E. coli* 0157:H7 (as a representative gram-negative bacterium) and *Streptococcus sobrinus* (as a representative gram-positive bacterium) were chosen as model organisms to optimize the PMA concentration and incubation time for treating cells. Log-phase cultures were split, with one half being subjected to 70% isopropanol resulting in complete loss of viability. Killing efficacy was examined by plating on the appropriate medium together with a viable positive control. PMA was added to final concentrations of 3, 30 or 240 µM. Whereas 30 µM corresponds to the PI concentration used in the BacLight live-dead staining kit (Molecular Probes), 240 µM equals the concentration of EMA used in previous studies[10,11,13,14]. FIGS. 3A and 3B shows the DNA yield of PMA treated culture aliquots in relation to the DNA yield from the corresponding untreated live or dead aliquots. Whereas 30 and 240 µM efficiently removed the DNA from dead cells, there was still a significant DNA background with 3 µM. The incubation time (1, 5 or 15 minutes) did not affect the genomic DNA yield to a great extent, although 15 minutes seemed to result in a moderate DNA loss in the case of exposing live *E. coli* 0157:H7 to 240 µM PMA. For the following experiments a PMA concentration of 50 µM and an incubation time of 5 minutes were chosen.

Example 4

Effect of PMA on Defined Ratios of Viable and Dead Cells

To elucidate the relationship between the proportion of viable cells, the DNA yield and the qPCR signals after PMA treatment, mixtures with defined ratios of viable and dead cells were used. An aliquot of *E. coli* 0157:H7 was subjected to heat treatment at 72° C. for 15 minutes resulting in a decrease in culturable cell counts to zero. Heat-killed cells were mixed with the untreated original culture in defined ratios with culturable viable representing 0, 0.1, 1, 10, 50 and 100% of the total bacterial cells, respectively (FIG. 4A). Whereas the DNA yields from mixtures I to VI were comparable without PMA treatment, increasing proportions of unstressed and viable cells led to a substantial increase in the genomic DNA yield (FIGS. 4B and 4C) and to decreasing $C_t$ values in qPCR (FIG. 4D) after PMA exposure. The highest $C_t$ value, i.e. greatest signal reduction, was observed for sample I containing only heat-killed *E. coli* 0157:H7. A plot of the natural logarithm of DNA yield (in percent of the highest value) versus $C_t$ values revealed a linear correlation with a $R^2$ value of 0.9742 of the corresponding trendline (FIG. 4E). This suggested that all DNA from live cells seemed to be amplifiable.

Example 5

Figure 5:
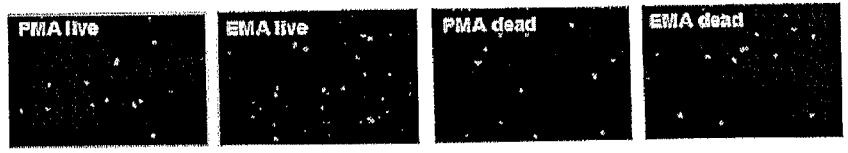
FIG. 5. Comparison of PMA and EMA membrane permeability characteristics and evaluation of the PMA live/dead assay with 9 bacterial species by fluorescence microscopy. (A) Microscopic comparison of dye uptake by live and dead *E. coli* O157:H7 stained with combinations of SYTO9/PMA and SYTO9/EMA (combined images), respectively. Green color indicates uptake of only SYTO9, red color indicates membrane permeability for PMA or EMA. (B) Effect of PMA and EMA treatment on the relative genomic DNA yield of live (white columns) and dead cells (grey columns) from 8 bacterial species and microscopic examination of membrane permeability after staining with either SYTO9/PMA or SYTO9/EMA. DNA yields measured in a TBS-380 fluorometer are shown in relation to the ones from the corresponding non-treated samples (defined as 100%). Genomic DNA was in addition visualized on agarose gels. Dyes were incubated at concentrations of 50 μM for 5 minutes in the dark before light exposure for 2 minutes. Error bars represent standard deviations from three independent replicates.
Figure 5:
Figure 5:
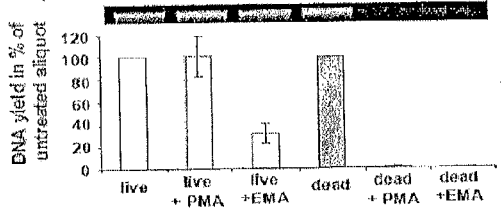
Figure 5:
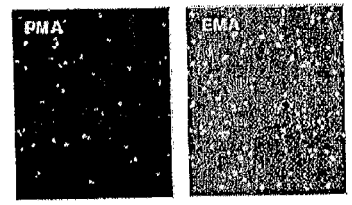
Figure 5:
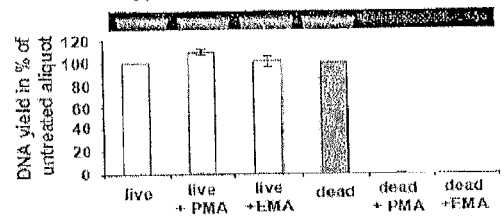
Figure 5:
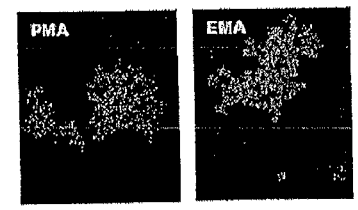
Figure 5:
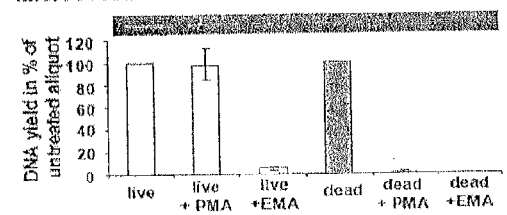
Figure 5:
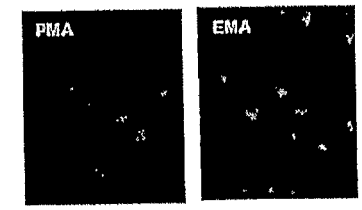
Figure 5:
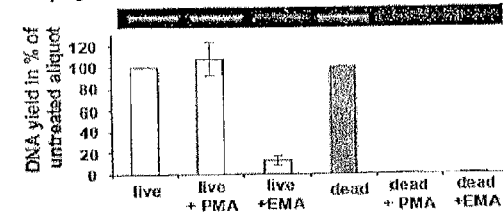

Comparison Between PMA and EMA and Evaluation of the PMA Live/Dead Assay with More Species The efficient removal of genomic DNA from dead cells by PMA and EMA treatment has been described for *E. coli* 0157:H7 in this and a previous study, respectively[10]. The difference between the two chemicals lies mainly in their selectivity. Whereas EMA treatment of live *E. coli* 0157:H7 led to a loss of more than 60% of the genomic DNA[10], PMA seems to circumvent this problem. The results were corroborated by microscopic observations using a combination of the dyes SYTO9/PMA or SYTO9/EMA (FIG. 5A). SYTO9 is known to stain all cells green, both with intact and compromised cell membranes. The green color mixes with the red color originating from EMA or PMA when cells take up the corresponding dye. Dead cells stained red with both PMA and EMA. Live cells, in contrast, displayed a difference in that a 5 minutes exposure with EMA led to red staining, whereas cells were still green after PMA treatment. This suggests that intact *E. coli* 0157:147 cell membranes can efficiently exclude PMA, but not EMA. This explains the loss of DNA from live cells after EMA treatment while PMA does not affect the yield.

Figure 5B:
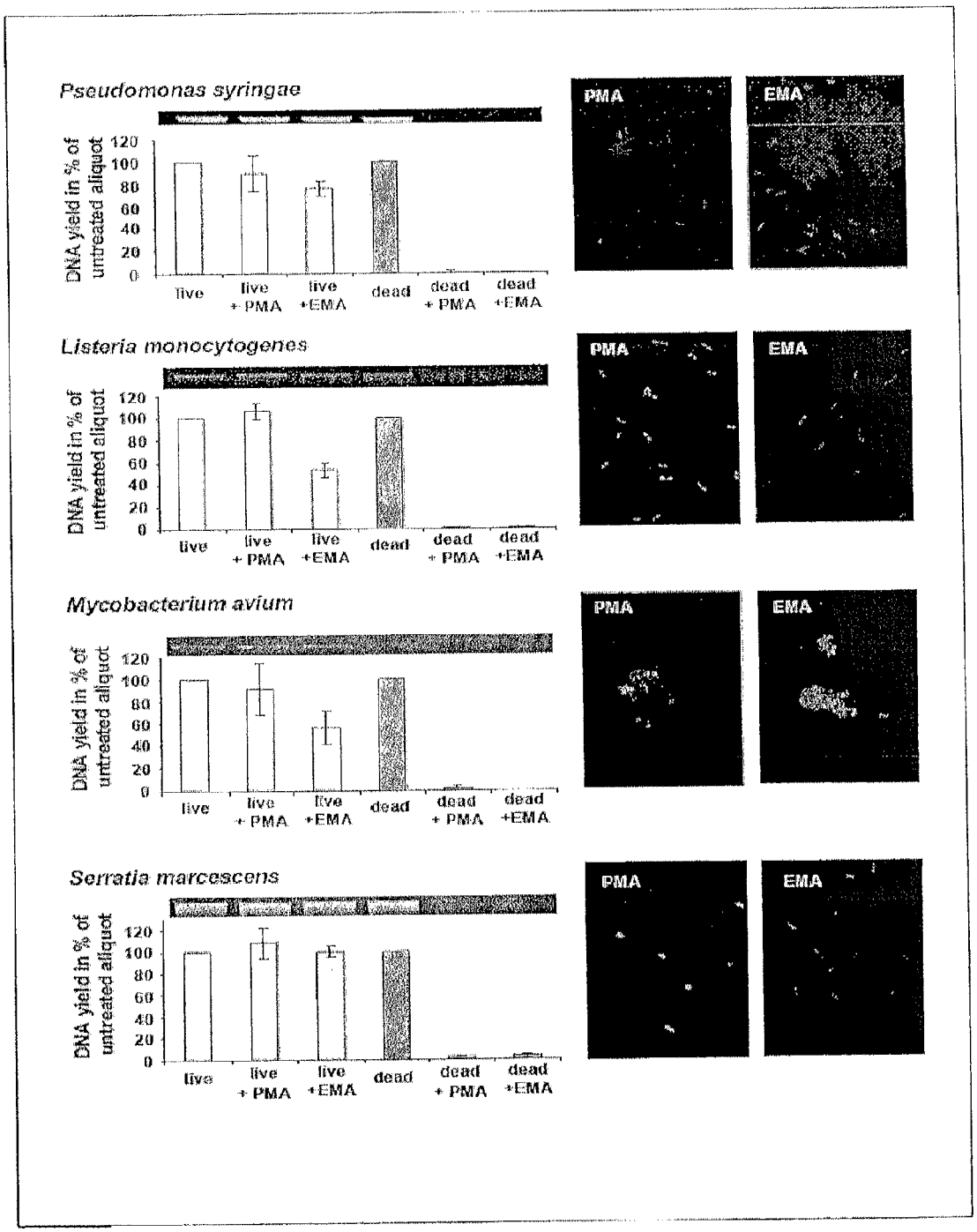

To further examine the application of the method to a wider spectrum of bacterial species, the PMA effect (in comparison with EMA) was tested on live and dead cells for the bacteria shown in Table 2. For all species tested, PMA did not affect the DNA yield from live cells, whereas the DNA from dead cells was efficiently removed during the DNA extraction procedure (FIG. 5B). EMA, on the other hand, was equally efficient in removing DNA from dead cells, but also partly reduced the DNA yield from live cells compared to untreated or PMA treated cells.

Dead cells from all species examined efficiently stained red both with PMA or EMA (data not shown). The microscopic pictures obtained from live cells treated with a combination of SYTO9/PMA or with a combination of SYTO9/EMA showed that PMA did not penetrate live cells in any of the species examined (FIG. 5B). EMA, on the other hand, could partly penetrate both dead and live cells (as seen by the red color) though the staining seemed to be more efficient in the case of dead cells. *Serratia marcescens*, *Salmonella typhimurium* and *Pseudomonas syringae* were the species most resistant to EMA uptake. Live cells of those species stained with SYTO9/EMA appeared green after 5 minutes.

This invention introduces a chemically modified version of propidium iodide with an azide group added to the phenanthridine ring allowing chemical crosslinkage to organic molecules upon short exposure to bright visible light. In analogy to PI, PMA does not seem to penetrate membranes of live cells, whereas it is efficiently taken up by permeabilized cells. Once inside cells, the dye intercalates into double-stranded nucleic acids. Upon binding, photo-induced crosslinkage renders the DNA insoluble and results in its loss during the DNA extraction procedure together with cell debris or PMA treatment may result in a modification of the DNA from cells with compromised membranes that results in inhibition of its PCR amplification. In the case of bacterial mixtures containing live and dead cells, the remaining DNA from live cells is amenable to further downstream analyses including quantification, qPCR or presumably microarray analysis.

Although selective analysis of DNA from live cells was first described for EMA using *E. coli* 0157:H7, *Salmonella typhimurium*, *Listeria monocytogenes* and *Camplylobacter jejuni* as model organisms[11,13,14], PMA has the advantage over EMA in terms of increased selectivity. Live cells of the majority of the various bacterial species examined in this study stained red with EMA using an EMA concentration about 4.8 fold below that used in previous studies[11,13,14]. This finding underlines that EMA cannot be considered to be generally membrane impermeable. Although it has been reported to exclusively penetrate only dead or damaged cells[11,13,14]

this may hold true only for selected bacterial species with short exposure times. The data presented here is in agreement with previous results showing that EMA treatment of live *E. coli* 0157:H7 cells leads to a loss of more than 60% of the genomic DNA during the DNA extraction procedure[10]. Moreover, EMA was recently shown to be unsuitable for live-dead differentiation of *Anoxybacillus*[12]. PCR inhibition was observed after treating viable *Anoxybacillus* with EMA and subsequent DNA extraction indicating that the agent penetrated the membrane of these cells and covalently cross-linked with the DNA during photolysis. As discussed herein, in addition, a significant loss of DNA due to EMA treatment of live cells for *Staphylococcus aureus, Listeria monocytogenes, Micrococcus luteus, Mycobacterium avium* and *Streptococcus sobrinus.*

The uptake of EMA by live cells is in agreement with studies examining the uptake of structurally identical ethidium bromide (EB) in wild-type *E. coli*. It was shown that EB is also taken up by viable cells although the net uptake reached only a few percent of that of fully permeabilized cells[4]. The reason is seen in the activity of a metabolically driven efflux pump. Metabolic inhibitors were shown to reduce efflux activity. Exposure of cells to cold shock (0 degrees for 30 minutes) in the presence of TRIS or EDTA led to a net uptake of EB similar to that of fully permeabilized cells[4]. For this reason EB is used in flow cytometric studies to identify metabolically active bacteria that are capable of active exclusion of the chemical[8,9].

Assuming the same mechanism for EMA, these findings would explain the observation that viable cells from log-phase cultures stained red with EMA. Even with active extrusion of EMA by such export systems, a considerable amount of dye might still remain in the cell. This would explain the significant loss of DNA from EMA-treated live cells compared to untreated or PMA treated cells. *Salmonella typhimurium* and *Serratia marcescens* seemed to be the only species of the ones examined that could be subjected to EMA treatment without any loss of DNA. The reasons for this might be more efficient efflux mechanisms or a less permeable cell membrane. They were also the species most resistant to EMA staining. *Pseudomonas syringae* seemed to stain very moderately with EMA, correlating with a certain loss of DNA during extraction. The obviously varying membrane permeability of different species, however, impedes a general application of EMA for live-dead differentiation in microbial diagnostics. PMA seems to have the important advantage over EMA of not penetrating live cells. The reason for the significantly higher selectivity of PMA is most probably associated with the higher charge of the molecule (EMA has one positive charge, PMA has two).

The present invention shows that the addition of the azide group to the PI molecule does not change its permeability characteristics. PI is the most commonly used dye for microscopic live-dead discrimination and has been extensively tested with a wide spectrum of bacteria including the ones used in this study. It is further widely used in flow cytometry[8,9,15]. It is worth mentioning that 4 physiological states are distinguished using fluorescent stains in flow cytometry: reproductively viable, metabolically active, intact and permeabilized cells[8]. Only the latter, the permeabilized cells, take up propidium iodide. In addition to not having an intact cell membrane, these cells are depolarized and de-energized. All but the permeabilized cells were shown to be capable of being resuscitated under adequate conditions, whereas cells positive to PI did not recover[8]. Excluding the DNA from the latter subpopulation would help limiting the analysis to the cells having the potential of recovery.

Example 6

Materials and Method for Testing Disinfectants

The aim of this study was to evaluate the applicability of the PMA method to monitor killing efficacy using different disinfection methods. Pure cultures of the common human pathogens *Salmonella typhimurium, Listeria monocytogenes, E. coli* 0157:H7 and *Mycobacterium avium* were used as model organisms. Treatment with hypochlorite, benzalkonium chloride (BAC), UV and heat were chosen as typical disinfection methods. Chlorine with its high oxidation capacity is one of the most commonly used antimicrobial disinfection methods in both drinking water and wastewater processing. It is also widely used for surface sanitation of foods and food processing environments and health care. Although the mechanism by which chlorine exerts its lethal effect has not been fully elucidated, it is accepted that chlorine exposure of bacterial cells leads to perforation of the cell membrane.

Hypochlorite Disinfection.

*Salmonella enterica* serovar Typhimurium (environmental isolate; Department of Microbiology, Montana State University) was grown in Luria Bertani (LB) broth for 12 hours at 37° C. in a shaker at 180 rpm. The cell density was adjusted to an $OD_{600}$ of 1.0 by dilution with LB broth before harvesting cells by centrifugation at 5000 g for 7 minutes. After removing the medium, the cell pellet was resuspended in an equal volume of phosphate buffered saline (PBS). Increasing volumes of a 1000 ppm sodium hypochorite stock solution (prepared by diluting 4-6% NaOCl; Fisher Scientific SS290-1) were added to 500 µl resuspended cell aliquots in 1.5 ml microcentrifuge tubes to achieve final concentrations between 5 and 40 ppm. The chlorine stock concentration was measured with a digital chlorine colorimeter kit (DPD method; LaMotte model DC 1100, Chestertown, Md.). Identical volumes of a sodium thiosulfate stock solution (1000 ppm) were added after a 15 minutes incubation (with occasional flipping) resulting in instantaneous dechlorination before harvesting cells (5000 g, 5 minutes). Approximately 40 ppm of thiosulfate was added to a non-chlorine exposed control sample to exclude an effect on viability by this chemical. The supernatant was carefully removed before rinsing the cell pellet with 1 ml of PBS. PBS was carefully removed after another centrifugation step and cells were resuspended in 500 µl PBS before plating serial dilutions on LB agar (overnight 20 incubation at 37° C.) and subjecting aliquots to PMA treatment.

Benzalkonium Disinfection.

*Listeria monocytogenes* (Department of Microbiology, Montana State University) was grown in Brain Heart Infusion (BHI) medium for 12 hours (30° C., 180 rpm) before adjusting the $OD_{600}$ to 1.0 by dilution with identical medium. A benzalkonium chloride (Acros Organics, Geel, Belgium) stock solution (5000 ppm) was added to 500 µl culture aliquots to achieve final concentrations in the range between 15 to 60 ppm. Cells were harvested after 30 minutes incubation by centrifugation (5000 g, 5 minutes). The supernatant was carefully removed and the cell pellets were resuspended in an identical volume of fresh BHI before plating serial dilutions on BHI agar and subjecting sample aliquots to PMA treatment.

UV Disinfection.

*E. coli* 0157:H7 (strain 932) was grown in LB medium for 12 hours at 37° C. and standardized to an $OD_{600}$ of 1.0. Approximately 15 ml of cells were harvested by centrifugation (5000 g, 5 minutes) and resuspended in the identical volume of PBS. The cell suspension was transferred into a 25 mm disposable Petri dish (lid off) and irradiated with short wave UV light (254 nm) using a Spectroline germicidal UV lamp EF 180 (Spectronics Corp., Westbury, N.Y.) placed at 20 cm over the cell suspension. Approximately 500 µl aliquots were taken after increasing exposure times and placed on ice until the last sample was taken before plating serial dilutions on LB agar (overnight incubation at 37° C.) and PMA treatment.

To study post-UV membrane integrity under the influence of residual chlorine contained in tap water, *E. coli* 0157:H7 ($OD_{600}$ of 1.0, prepared as described above) was UV-exposed for 5 minutes. Two aliquots of 20 ml cell suspension (approximately $1.5 \times 10^9$ cells/ml) were each filled in a sterile bacterial cage (23) sealed with 0.1 µm Supor®-100 membrane filters (Pall, Ann Arbor, Mich., USA) on both sides. Filled cages were submerged in a flow through reactor with a total volume of 1.0 liter regular tap water and with a water turnover of 1.0 volume per hour. Residual chlorine concentration was measured as described before. Samples were taken every 24 hours for up to 120 hours taken starting at time point zero and either treated with PMA or not followed by genomic DNA extraction.

To study post-UV membrane integrity under the influence of heat, an *E. coli* 0157:H7 suspension (prepared as before) was UV-treated for 5 minutes and exposed to heat stress at 58° C. in a regular lab thermo block in 0.5 ml aliquots. Samples were taken every hour from time point zero up to 5 hours and were either treated with PMA or not, followed by genomic DNA extraction.

Heat Disinfection.

*Mycobacterium avium* complex (strain W2001) was grown in Middlebrook 7H9 broth (Difco Laboratories, Detroit, Mich.) supplemented with 0.2% (w/v) glycerol and 2% Bacto Middlebrook ADC enrichment (Difco) at 37° C. (100 rpm). The $OD_{600}$ was adjusted to 0.3 by dilution with the identical medium. Culture aliquots of 125 µl were transferred into 0.2 ml PCR tubes and exposed to different temperatures for 15 minutes using a PCR machine (Eppendorf EP gradient). Aliquots were combined to give volumes of 500 µl before PMA treatment and further processing. Serial dilutions of non-PMA treated aliquots were plated on Middlebrook 7H10 agar supplemented with 10% OADC (both from Difco) and 0.5% (w/v) glycerol and grown for approximately 10 days at 37° C.

PMA Cross-Linking.

PMA (phenanthridium, 3-amino-8-azido-5-[3-(diethylmethylammonio)propyl]-6-phenyl dichloride; Biotium, Inc., Hayward, Calif.) was dissolved in 20% DMSO to create a stock concentration of 20 mM and stored at −20° C. in the dark. Approximately 1.25 µl PMA were added to 500 µl culture aliquots to final concentrations of 50 µM. Following an incubation period of 5 minutes in the dark with occasional mixing, samples were light-exposed for 2 minutes using a 650-W halogen light source placed 20 cm from the sample tubes. During exposure, samples were placed on ice to avoid excessive heating. After photo-induced crosslinking, cells were pelleted at 5000 g for 5 minutes prior to DNA isolation.

DNA Isolation and Quantification.

Genomic DNA was extracted using the Qbiogene soil kit (Qbiogene, Carlsbad, Calif., USA). Cell lysis of pure cultures was achieved by bead beating using a FastPrep machine (Qbiogene) for 30 seconds at a speed setting of 5 m/s. Cell debris were removed by centrifugation at 13,000 g for 5 minutes, both directly after bead beating and after addition of 250 µl of PPS solution (provided in the kit) to the supernatant after bead beating. DNA was eluted with a volume of 120 µl DES buffer (provided by the kit) and visualized on ethidium bromide stained 1% agarose gels. About ten percent of the total corresponding eluate volumes were loaded on agarose gels.

Quantitative PCR.

Relative quantitative PCR and data analysis were performed with a SmartCycler II (Cepheid, Sunnyvale, Calif.). Cycle threshold ($C_t$) values were automatically calculated by the SmartCycler software using a 30 fluorescence unit threshold. For all experiments, 1 µl of extracted genomic DNA was added to 24 µl of PCR mixture containing Sybr Green PCR Master Mix (Applied Biosystems, Foster City, Calif., USA) and 10 pmol of each primer. Primers used for quantification are given in Table 1. For amplification of *E. coli* 0157:H7 stx1 genes the 25 µl PCR mixture was supplemented with 1.5 µl of 25 mM $MgCl_2$. The cycling parameters for quantification of *Salmonella typhimurium* were: 9 minutes at 95° C. (initial polymerase activation and denaturation) followed by 45 cycles of 20 sec at 95° C., 30 sec at 60° C. and 25 sec at 72° C.; for *Listeria monocytogenes:* 9 minutes at 95° C. followed by 45 cycles of 20 sec at 95° C., 20 sec at 55° C. and 15 sec at 72° C.; for *E. coli* 0157:H7: 9 minutes at 95° C. followed by 45 cycles of 20 sec at 95° C., 25 sec at 55° C. and 25 sec at 72° C.; for *Mycobacterium avium:* 9 minutes at 95° C. followed by 45 cycles of 30 sec at 95° C., 20 sec at 60° C. and 20 sec at 72° C. For melt curve analysis the temperature was increased in 0.2° C. increments from 60 to 94° C.

Example 7

Results from the Hypochlorite Disinfection

Figure 6:
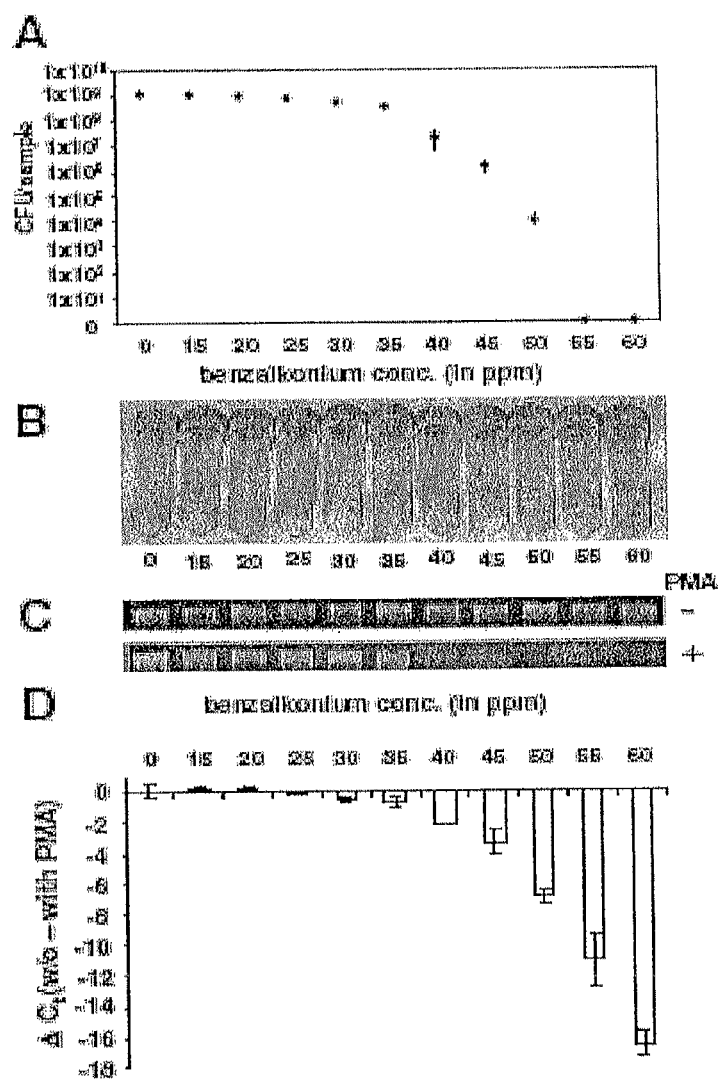
FIG. 6. Monitoring exposure of *Salmonella* to increasing concentrations of hypochlorite (in ppm). Error bars represent standard deviations from three independent replicates. (A) Loss of culturability as determined by plate counts. C stands for the control exposing cells to 40 ppm thiosulfate used for dechlorination of the sample with the highest hypochlorite concentration. (B) Lysis matrix tubes with pelleted cell debris for increasing hypochlorite concentrations after previous PMA treatment. Lysis matrix tubes are shown after centrifugation for 5 minutes at 14,000 g with the cell debris facing upward. (C) Genomic DNA from non-PMA treated (top) or PMA treated (bottom) cells as visualized on an agarose gel. (D) Signal reduction as determined by qPCR detecting relative differences in invasin A gene (invA) copies. $C_t$ values derived from PMA-treated cultures were subtracted from the corresponding $C_t$ values for untreated cultures.

Aliquots of a *Salmonella* culture were subjected to increasing concentrations of hypochlorite. Following a 15 minutes incubation time, the chlorine was inactivated by addition of thiosulfate resulting in instantaneous dechlorination. Plate counts suggested only minor effect of concentrations of up to 10 ppm (FIG. 6A). Increasing the concentration resulted in a sharp drop in colony counts with concentrations of 25 ppm and higher resulting in complete loss of culturability. A thiosulfate control (with 40 ppm of thiosulfate, but with no hypochlorite added) showed colony counts comparable to the sample with neither chemical added excluding an effect of thiosulfate on culturability. Extraction of genomic DNA from PMA-treated samples showed an increasingly red cell debris pellet for increasing disinfectant concentrations starting at around 25 ppm (FIG. 6B). The most intense red color was visible at a hypochlorite concentration of 40 ppm. The resulting DNA was visualized on an ethidium bromide stained agarose gel: DNA extracted from non-PMA treated cells showed similar yields for all samples whereas PMA treatment resulted in increasingly less visible DNA with increasing concentrations of hypochlorite (FIG. 6C). This tendency was reflected in qPCR detecting differences in invasion A gene (invA) copy numbers. Subtracting the $C_t$ values of PMA-treated aliquots from the corresponding non-treated aliquots showed that increasing hypochlorite concentrations resulted in increasingly strong signal reductions (FIG. 6D). Signal reduction started to be significant at a concentration of 20 ppm hypochlorite. The strongest signal reduction of around 14 amplification cycles was observed with 40 ppm hypochlorite treatment.

These data indicate that the cell envelope appears to be a plausible site of chemical interaction[18]. The observation of chlorine-induced alterations made the cytoplasmic membrane a possible key target[19]. Thus, chlorine has a direct impact on cell membrane integrity, therefore allowing the application of PMA to monitor disinfection.

Example 8

Results from the Benzalkonium Chloride Disinfection

Benzalkonium chloride (BAC) is a mixture of alkylbenzyl dimethylammonium chlorides of various alkyl chain lengths and is a widely used quaternary ammonium compound[20]. This synthetic biocide is found in many household cleaners/sanitizers and is used extensively for surface disinfection of the meat and dairy processing environment in the food industry, but also as an antiseptic in medicine. Quaternary ammonium compounds are known to act on general membrane permeability causing cytolytic leakage at low concentrations and general coagulation in the bacterial cytoplasm at high concentrations.

Figure 7:
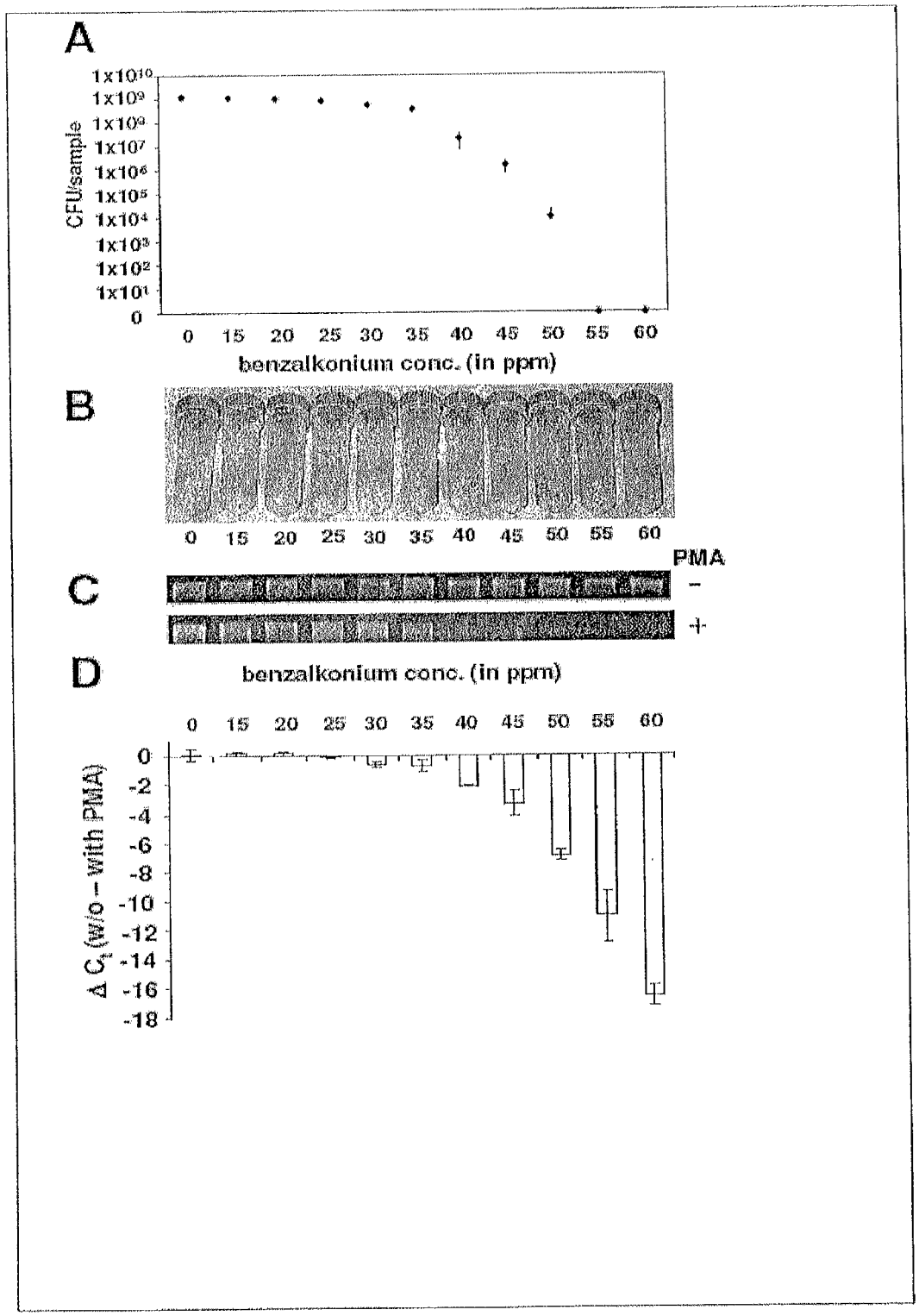
FIG. 7. Monitoring exposure of *Listeria monocytogenes* to increasing concentrations of benzalkonium chloride (in ppm). Error bars represent standard deviations from three independent replicates. (A) Loss of culturability as determined by plate counts. (B) Lysis matrix tubes with pelleted cell debris for increasing benzalkonium concentrations after previous PMA treatment. Lysis matrix tubes are shown after centrifugation for 5 minutes at 14,000 g with the cell debris facing upward. (C) Genomic DNA from non-PMA treated (top) or PMA treated (bottom) cells as visualized on an agarose gel. (D) Signal reduction as determined by qPCR detecting relative differences in listeriolysin O gene (hly) copies. $C_t$ values derived from PMA-treated culture aliquots were subtracted from the corresponding $C_t$ values of untreated cultures.

Listeria monocytogenes was exposed to increasing concentrations of BAC for 30 minutes. Concentrations exceeding 30 ppm increasingly reduced culturability (FIG. 7A). No colonies were obtained with concentrations of 55 and 60 ppm benzalkonium. Genomic DNA extraction from PMA treated samples resulted in increasingly red cell debris pellets with increasing disinfectant concentration (FIG. 7B). The loss of culturability was further accompanied by an increased fading of DNA bands on an agarose gel following PMA treatment and DNA extraction whereas DNA band intensities of non-PMA treated cells were not affected by BAC exposure (FIG. 7C). Simultaneously, qPCR detecting differences in listeriolysin O gene (hly) copy numbers showed an increasing signal reduction, when comparing $C_t$ values from non-PMA treated and PMA treated aliquots (FIG. 7D). The greatest signal reduction of around 17 PCR cycles was obtained with 60 ppm BAC.

These data indicate that treatment of Listeria monocytogenes with BAC revealed a very good correlation between loss of culturability and loss of membrane integrity as measured by plate counts and signal reduction in qPCR, respectively. In contrast to chlorine, both 'viability' indicators dropped simultaneously with increasing disinfectant concentration. This might be because the mode of action of BAC is primarily based on membrane damage (such as disruption of intermolecular interactions and dissociation of membrane bilayers both compromising permeability control and inducing leakage), whereas in the case of chlorine multiple other, non-membrane related factors might contribute to cell death.

Example 9

Results from UV Disinfection

UV treatment is widely used for drinking water disinfection and is generally considered to exert its lethal action through DNA damage[21]. Membrane damage might, however, be an indirect consequence of general cell deterioration. Studying the effect of PMA treatment on UV-exposed cells was intended to shed light on the effect of UV on membrane integrity and served as further proof of principle.

Figure 8:
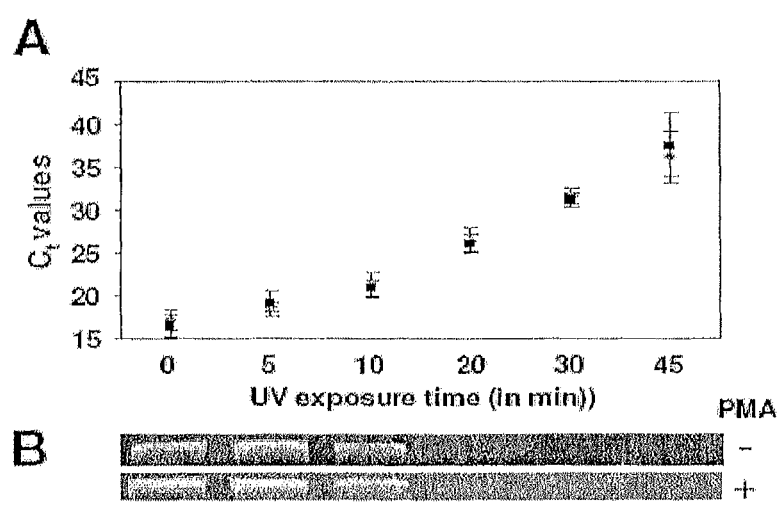
FIG. 8. Monitoring UV-exposure of E. coli 0157:H7 for increasing time periods. Error bars represent standard deviations from three independent replicates. (A) Increase of $C_t$ values from PMA and non-PMA treated aliquots determined by qPCR detecting relative differences in Shiga-like toxin 1 gene (stx1) copies. (B) Genomic DNA from non-PMA treated (top) and PMA treated (bottom) cells visualized on an agarose gel.

Exposure of E. coli O157:H7 to UV light, under the conditions described above, led to a complete loss of culturability within 5 sec. This short UV exposure time did not, however, affect PMA uptake by these cells (compared to non-exposed cells) as indicated by the white color of pelleted cells. $C_t$ values after PMA treatment compared with identical but non-UV exposed samples detecting differences in Shiga-like toxin 1 gene (stx1) copies (data not shown), were identical. Exposure for longer time periods resulted in an increase in $C_t$ values for both PMA treated and non-PMA treated samples (FIG. 8A). The increasing Ct values correlated with an increased fading of genomic DNA visualized on an agarose gel, again independent of PMA treatment (FIG. 8B). No genomic DNA could be seen on the gel by eye for samples exposed to UV for 30 minutes and longer.

The fact that PMA treatment of exposed cells was not able to differentiate between culturable and non-culturable cells and that the increase in $C_t$ values with increasing exposure times was independent of PMA treatment, led to the conclusion that cell damage did result from cell membrane permeability. Only long UV exposures exceeding 45 minutes resulted in increasingly red staining of PMA-treated cells and presumed membrane damage (data not shown). However, such long exposure times are rarely applied in industry.

To examine whether UV exposure affects membrane integrity post-UV in the presence of other stress factors affecting membranes, untreated (live) and UV-killed E. coli O157:H7 were exposed to tap water containing a residual chlorine concentration of 0.5 ppm. Samples were taken every 24 hours for up to 120 hours starting at time point zero and were either treated with PMA or not. A linear increase in $C_t$ values over time was observed for both live and UV-killed cells (data not shown). In both cases PMA treatment resulted in increasing $C_t$ value differences over time compared to non-PMA treated samples. In the case of non-UV exposed cells this correlated with a loss of culturability. The fact that increasing PMA uptake (presumably caused by chlorine-induced membrane damage) was independent of UV exposure led to the conclusion that in this experiment the membranes of UV-killed cells did not deteriorate any faster than the ones of non-UV exposed cells. We therefore examined whether subjecting UV-killed cells to sublethal heat stress (58° C.) would lead to expedited membrane breakdown compared to non-UV-exposed live cells. Samples were taken every hour starting from time point zero up to 5 hours. In this experiment, we observed a PMA-induced increase in $C_t$ values for UV-killed cells over time, but not for non-UV exposed cells (data not shown). The difference in $C_t$ values was moderate with an increase of around 2 cycles for the sample heated for 5 hours. This finding correlated with the observation that pellets of UV-killed cells were increasingly stained reddish by PMA whereas pellets of live cells were still white even after 5 hours of heat exposure.

Whereas the PMA method seems to be able to detect chlorine or BAC-caused membrane damage after disinfection, cell damage caused by UV could not be monitored directly after UV-exposure. This is not surprising considering that the main cellular targets of short wave UV-C light are nucleic acids and not the membrane[22,23]. We observed that only long UV exposures exceeding 45 minutes led to red staining of cells meaning those cells took up PMA more readily than non-UV exposed cells. Such prolonged exposure times obviously led to a breakdown of membrane integrity allowing PMA uptake either as a direct consequence of UV exposure or indirectly through general breakdown of cell integrity. The resulting increased PMA uptake, however, does not or only very moderately affects $C_t$ values in comparison to non-PMA treated samples as the long UV exposure already decreased DNA amplifiability to a minimum. Interestingly, the increase in $C_t$ values for increasing UV exposure times correlated with increasing loss of fluorescence of the ethidium bromide stained agarose gel. In contrast to the chlorine and BAC experiments, fading band intensity is most probably due to DNA damage including strand breaks and crosslinks. Normally the fluorescence of bound ethidium bromide is proportional to the concentration of duplex DNA. It has been reported that ethidium bromide does not bind, however, to pyrimidine dimers (whose formation results in conformational changes), hydrated bases or single-stranded regions caused by UV light[24]. Therefore the accumulation of DNA damage increasingly prevents intercalation of ethidium bromide into the DNA leading to a loss of fluorescence. This 'ethidium fluorescence assay' has been established for sensitively and conveniently measuring DNA damage caused by radiation[25]. The same factors decreasing ethidium fluorescence would also inhibit PCR amplification. To examine whether UV exposure affects membrane integrity post-UV in the presence of other stress factors affecting membranes, UV-killed E. coli 0157:H7 cells were compared to non-UV exposed cells concerning their resistance to chlorinated tap water and to sublethal temperatures (58° C.). Tap water exposure in a flow-through reactor resulted in comparable cell membrane damage for both UV- and non-UV exposed cells increasing over time. This finding was surprising as faster membrane deterioration for UV-killed cells was expected due to the lack of repair. The heat exposure, on the other hand, resulted in increased PMA uptake over time for the UV-exposed cells compared to non-UV exposed cells. The red staining of the cells was, however, only moderate even after 5 hours of heat exposure. This observation was reflected in a moderate qPCR signal reduction of around 2 cycles. Although these results suggested that UV-killed cells are surprisingly resistant to membrane deterioration, this does not exclude the possibility that the simultaneous combination of multiple post-UV stress factors might make them more susceptible to membrane damage due to the lack of repair. Expedited membrane permeabilization would allow the application of the PMA method in post-UV treatment.

Example 10

Results from Heat Disinfection

Heat disinfection was chosen for its practicality. Killing bacteria or reducing bacterial viability with elevated temperatures might be the oldest and most commonly applied disinfection method. It was shown in a prior study that PMA treatment of bacteria exposed to a lethal dose of heat leads to the selective signal loss of DNA from these cells[26,27]. The heat gradient in the range from sublethal to lethal temperatures studied here was intended to elucidate and refine the sensitivity of the PMA method.

Figure 9:
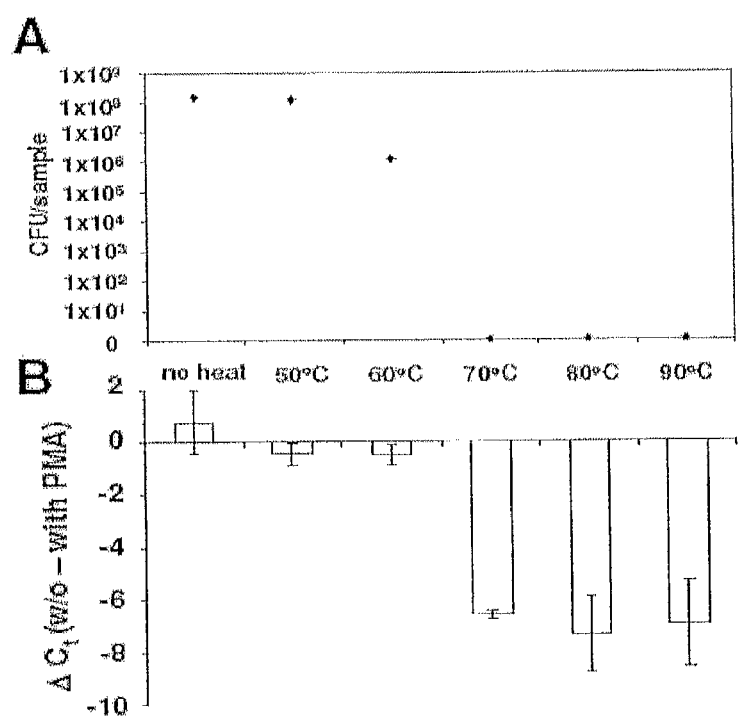
FIG. 9. Monitoring exposure of Mycobacterium avium to different temperatures for 15 minutes. Error bars represent standard deviations from three independent replicates. (A) Loss of culturability as determined by plate counts. (B) Signal reduction as determined by qPCR detecting relative differences in trehalose synthase gene (treS) copies. $C_t$ values derived from PMA-treated culture aliquots were subtracted from the corresponding $C_t$ values of untreated cultures.

Subjecting *Mycobacterium avium* to increasing heat stress for 15 minutes resulted in a dramatic loss of culturability around 60° C. (FIG. 9A). No colonies were obtained after exposure to temperatures of 70° C. and higher. This correlated well with a strong increase in qPCR signal reduction detecting differences in trehalose synthase gene (treS) copy numbers between 60° C. and 70° C. (FIG. 9B). Temperatures exceeding 70° C. did not lead to any further significant increase of $C_t$ values after PMA treatment. DNA yields obtained from DNA extraction were too low to be visualized on ethidium bromide stained agarose gels (data not shown). The low DNA concentration might also be the reason why lysis matrix tubes did not show red pellets after centrifugation in the case of PMA-treated heat-killed cells (data not shown).

Evidence for damage to bacterial membranes by heat has been provided by reports about heat-induced leakage of intracellular substances and loss of lipopolysaccharides. Elevated temperatures have been reported to induce outer membrane membrane blebbing and vesiculation for *Escherichia coli*. This study confirmed that heat has a direct effect on membrane permeability allowing PMA to enter the cell. A good correlation between loss of culturability and qPCR signal reduction could be observed. The most dramatic change occurred in the temperature range between 60° C. and 70° C.

Thus, this study shows that PMA treatment in combination with qPCR is successful in monitoring the germicidal action of disinfectants directly affecting membrane permeability. This technology effectively limits DNA-based molecular diagnostics to cells with intact cell membranes instead of indiscriminately amplifying DNA from all cells including permeabilized cells. The PMA treatment is rapid, simple and easy-to-use and can be combined with established downstream DNA-detection assays. In addition to the disinfection methods described here, PMA uptake and monitoring of killing efficacy by qPCR has also been successfully applied to cells killed by isopropanol exposure[26]. The method is limited, however, to disinfectants causing membrane damage. Although UV-C light does lead to a loss of amplifiability (probably caused by DNA damage), PMA treatment did not affect $C_t$ values. Only very long UV exposure times might lead to membrane damage allowing PMA uptake. Such long exposure times are unlikely to be relevant in terms of germicidal treatment as cell death can be assumed to occur at much shorter exposure times. However, it can be assumed that cell death and general loss of cell integrity eventually leads to membrane damage making these cells amenable for PMA uptake. The potential of PMA for monitoring of other disinfection methods including treatment with hydrogen peroxide, phenol, aldehydes, surfactants, physical pressure or heavy metals like silver and copper and the correlation to traditional cultivation-based screening remains to be tested.

Example 11

Materials and Methods for Detecting Viable Cells in a Mixed Bacterial Community

Four experiments were performed to study the usefulness of PMA treatment of mixed bacterial communities comprising both intact and compromised cells in combination with end-point PCR: (1) Profiling of defined mixtures of live and isopropanol-killed cells from pure cultures of random environmental isolates; (2) Profiling of a waste water treatment plant influent sample spiked with defined ratios of live and dead cells; (3) Profiling of selected environmental communities and (4) Profiling of a water sediment sample exposed to increasing heat stress. Regions of 16S rRNA genes were PCR-amplified from extracted genomic DNA and PCR-products were analyzed using denaturing gradient gel electrophoresis (DGGE).

Defined Mixtures of Bacterial Environmental Isolates.

Figure 10:
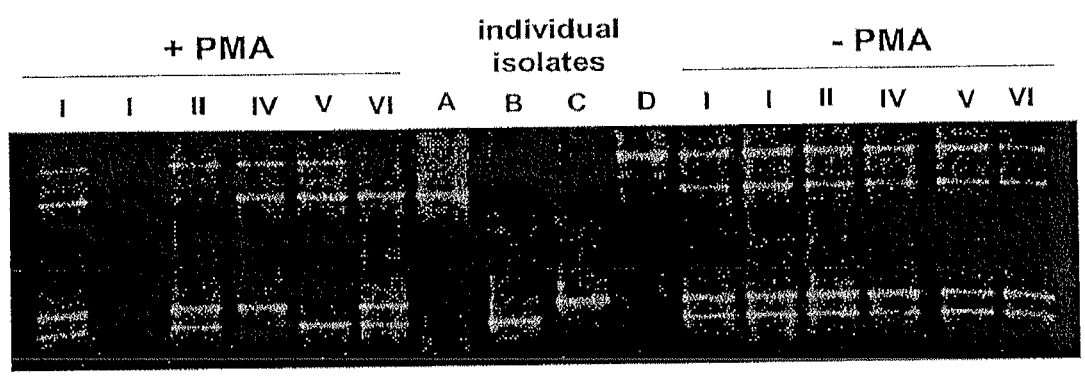
FIG. 10. Effect of PMA on genotypic profiles of defined bacterial mixtures of viable and dead bacterial duck pond isolates. Blast search results of partial 16S rRNA sequences obtained from individual isolates are given together with degrees of similarity to their corresponding nearest phylogenetic neighbor. Identical volumes of untreated or isopropanol-killed pure culture aliquots were mixed according to the scheme given. Mixtures I-VI were either PMA treated or not followed by genomic DNA extraction and amplification of partial 16S rRNA genes. DGGE profiles of PCR products obtained from mixtures are compared to the bands obtained from pure individual isolates.

Water samples from the Montana State University duck pond were diluted 10 fold with phosphate buffered saline (PBS) and spread on tryptic soy agar (TSA) plates. Plates were incubated at room temperature for 5 days. Randomly picked colonies were restreaked. Single colonies were grown in tryptic soy broth (TSB) in a shaker at 180 rpm at room temperature to obtain pure cultures. These were later identified by sequencing of cloned 16S rRNA genes. Optical densities were adjusted to an $OD_{600}$ of 1 by dilution with TSB. Cells in 500 µl aliquots were killed by exposure to isopropanol (final concentration 70%) for 10 minutes. Isopropanol was removed by harvesting cells using centrifugation at 5000×g for 5 minutes and removal of supernatant. Pellets of killed cells were resuspended in 500 µl PBS. Aliquots of 125

µl of either untreated or isopropanol exposed cells of the different species were mixed according to FIG. 10 to give a final volume of 500

Spiking of a WWTP Influent Sample with Defined Ratios, of Live and Dead *E. coli* 0157:H7.

Waste water influent samples were collected at the waste water treatment plant (WWTP) in Bozeman in 100 ml aliquots. Bacteria were harvested from the waste water by centrifugation at 5,000 g for 10 minutes. The supernatant was removed by decanting and pipetting, leaving the last 7 ml. After resuspension, 434 µl aliquots were distributed into 1.5 ml microcentrifuge tubes for subsequent spiking. *Escherichia coli* 0157:H7 (strain 932) was grown to log phase in Luriani-Bertani (LB) medium at 37° C. on a shaker at 280 rpm. The culture was diluted to an $OD_{600}$ of 1 by dilution with LB. Cells were harvested by centrifugation and resuspended in PBS. 500 µl aliquots in microcentrifuge tubes were killed by exposure to 75° C. for 15 minutes using a standard laboratory heat block. As shown by plating, this heat treatment reduced culturability to zero. For the spiking experiment $10^7$ total cells (confirmed by plate counts of $10^{-6}$ diluted aliquots) of different ratios of live and killed cells (in a volume of 66 µl) were added to the 434 µl of concentrated waste water to give a total volume of 500 µl.

Selected Environmental Microbial Communities.

Three microbial communities of municipal waste water, estuarine benthic mud and marine sediment were used. Water samples were collected from an aerated sludge basin at the WWTP Bozeman in 100 ml aliquots. Bacteria were harvested from the waste water by centrifugation at 5,000 g for 10 minutes. The supernatant was removed by decanting and pipetting except for the last 3 ml. Aliquots of 500 µl were distributed to microcentrifuge tubes.

Estuarine benthic mud and marine sediment together with salt water (Gulf Breeze, Fla.) were collected in 50 ml tubes. Samples were mixed by inverting multiple times before allowing mud particles, stones and sand to settle for 1 minute. 1 ml of the turbid supernatant was transferred to clean tubes and cells were harvested by centrifugation at 5000 g for 5 minutes. Pellets were resuspended in 1.0 ml PBS and subsequently split in two 500 µl portions for each sample. One aliquot was subjected to PMA treatment (see below), the other was not.

Exposure of a water reservoir sediment sample to increasing heat stress. Sediment samples were collected from a non-light exposed water reservoir. Approximately 1.0-2.0 g of sample (dry weight) were suspended in 5 ml of the same water by pipetting, vortexing (for 10 seconds) and sonication (for 5 seconds, low setting on a T25 Si machine from Janke & Kunkel GmbH, Staufen, Germany) for resolution of cell clumps. Identical aliquots of 500 µl were distributed in microcentrifuge tubes and exposed to different temperatures in a laboratory heat block for 15 minutes.

PMA Cross-Linking.

PMA (phenanthridium, 3-amino-8-azido-5-[3-(diethylmethylammonio)propyl]-6-phenyl dichloride; Biotium, Inc., Hayward, Calif.) was dissolved in 20% DMSO to create a stock concentration of 20 mM and stored at $-20°$ C. in the dark. Typically 1.25 µl PMA were added to 500 µl culture aliquots to final concentrations of 50 µM. Following, an incubation period of 5 minutes in the dark with occasional mixing, samples were light-exposed for 2 minutes using a 650-W halogen light source placed 20 cm from the sample tubes. During exposure, samples were placed on ice to avoid excessive heating and gently shaken. After photo-induced crosslinking, cells were pelleted at 5,000 g for 5 minutes prior to DNA isolation.

Genomic DNA Extraction.

Genomic DNA was extracted using the Qbiogene soil kit (Qbiogene, Carlsbad, Calif., USA). Cell lysis was achieved by bead beating using a FastPrep machine (Qbiogene) for 30 seconds at a speed setting of 5.5 m/s. Cell debris were removed by centrifugation at 13,000 g for 5 minutes, both directly after bead beating and after addition of 250 µl of PPS solution (provided in the kit) to the supernatant after bead beating. DNA was eluted with a volume of 120 µl DES buffer (provided in the kit).

PCR Amplification of 16S rRNA Genes.

Figure 11:
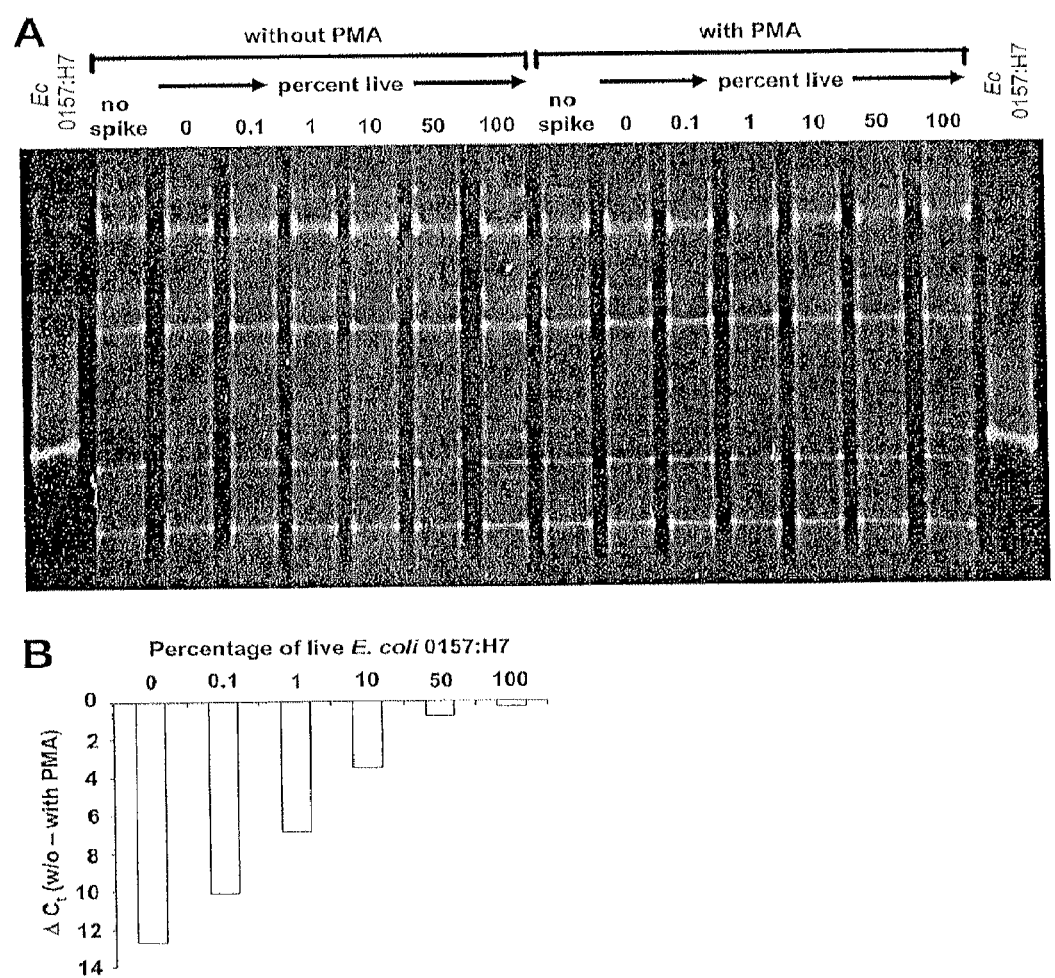
FIG. 11. Analysis of WWTP influent samples spiked with $10^7$ E. coli 0157:H7 cells with increasing proportions of live cells. (A) DGGE profiles of samples that were subjected to PMA-treatment or not. 16S rRNA gene profiles from spiked samples are compared to the corresponding profiles from unspiked samples. The band obtained from a pure culture of E. coli 0157:H7 serves as a reference. (B) Signal reduction as determined by qPCR detecting relative differences in shiga toxin 1 gene (stx1) copies. $C_t$ values derived from PMA-treated spiked samples were subtracted from the corresponding $C_t$ values of non-PMA treated spiked samples. The signal reduction shown here is the average of two qPCR runs using the same template.

Approximately 5 ng of extracted genomic DNA served as a template for amplification of an internal fragment of the 16S rRNA coding gene using 10 pmol each of primers 1070F (5'-ATGGCTGTCGTCAGCT-3'; SEQ ID NO 12) and 1392R (5'-ACGGGCGGTGTGTAC-3'; SEQ ID NO 13); 1392R had a GC clamp at its 5' end (5'-CGCCCGCCGCGCCCCGCGC-CCGGCCCGCCGCCCCCGCCCC-3'; SEQ ID NO 14). PCR reactions were performed in a total volume of 50 µl containing 1×PCR Master Mix (Promega, Madison, Wis., USA). Cycling parameters shared by all experiments were: initial denaturation for 2 minutes at 95° C.; varying number of cycles of 30 s at 95° C., 30 s at 55° C., and 30 s at 72° C.; and a 5-minutes final elongation step at 72° C. The number of amplification cycles varied between experiments: 28 cycles for the amplification of 16S rRNA from defined 4-species mixtures (FIG. 10), 30 cycles for DNA amplification from spiked and unspiked WWTP influent samples (FIG. 11), 25 cycles for DNA amplification from aerated waste water samples and 30 cycles for the estuarine benthic and marine sediment samples (all FIG. 12). For amplification of DNA extracted from a water reservoir sediment sample a 2-step approach was chosen: 3.0 µl from a PCR reaction with 10 cycles were used as template for a second PCR reaction with 25 cycles.

16S rRNA genes from duck pond isolates for cloning and sequencing were amplified using primer 27F (5'-AGAGTTTGATCCTGGCTCAG-3'; SEQ ID NO 15), the universal primer 1392R (5'-ACGGGGCGGTGTGTAC-3'; SEQ ID NO 16) and about 10 ng of the corresponding genomic DNA as template. The PCR mixture was the same as described before. The cycling parameters were: 2 minutes at 94° C. (initial denaturation) followed by 30 cycles of 30 sec at 94° C., 30 sec at 55° C. and 90 sec at 72° C. followed by a 7 minutes final elongation step at 72° C.

Cloning and Sequencing of 16S Ribosomal DNA (rDNA) PCR Products.

PCR products obtained from the amplification of individual duck pond isolates were separated on 0.8% agarose gels followed by excision of bands of app. 1,400 by in length. The DNA was purified using the QIAquick gel extraction kit (QIAGEN, Valencia, Calif.) following the manufacturer's instructions. DNA products were cloned using a TOPO TA Cloning® kit (Invitrogen, Carlsbad, Calif., USA) in accordance with the manufacturer's instructions. Ligation mixtures were used to transform competent *E. coli* TOP10 cells (supplied with the cloning kit). Recombinants were selected by using LB agarose plates containing 50 µg of kanamycin *E. coli* transformants carrying plasmids with 16S rDNA inserts were grown overnight in LB broth with 50 µg of kanamycin $ml^{-1}$. Plasmid DNA was isolated using a QIAprep spin miniprep kit (QIAGEN) according to the manufacturer's instructions. Sequencing was carried out at the Genomics Technology Support Facility (Michigan State University, East Lansing, Mich., USA) with the M13F-20 primer (5'-GTAAAACGACGGCCAG-3' SEQ ID NO 17). Sequences of around 700 bases were entered into the BLAST search program of the National Center for Biotechnology Information (NCBI) in order to obtain closely related phylogenetic sequences.

Denaturing Gradient Gel Electrophoresis.

100-150 ng of PCR products were analyzed using DGGE. Gels had 8% polyacrylamide and a denaturation gradient of 30% to 70%, where 100% denaturant is defined as 7 M urea and 40% formamide (all reagents were from Sigma-Aldrich, St. Louis, Mo., USA). Electrophoresis was carried out at 60 V for 16 h using a DCode system (Bio-Rad, Hercules, Calif., USA). Gels were stained with SybrGold (Molecular Probes, Inc., Eugene, Oreg., USA) and documented using a Fluor Chem 8800 fluorescence imager (Alpha Innotech, Inc., San Leandro, Calif., USA).

Quantitative PCR.

For relative quantification of *E. coli* 0157:H7 used for spiking a waste water sample, 1 µl of extracted genomic DNA was added to 24 µl of PCR mixture containing 1× Power SYBR® Green PCR Master Mix (Applied Biosystems, Foster City, Calif., USA), 10 pmol of primers stx1-forward (5'-GACTGCAAAGACGTATGTAGATTCG-3'; SEQ ID NO 1) and primer stx1-reverse (5'-ATCTATCCCTCTGACAT-CAACTGC-3'; SEQ ID NO 2) and 1.5 mM $MgCl_2$ (in addition to the $MgCl_2$ contained in the Master Mix). Quantitative PCR and data analysis were performed with a SmartCycler II (Cepheid, Sunnyvale, Calif.). Cycle threshold ($C_t$) values were automatically calculated by the SmartCycler software using a 30 fluorescence unit threshold. The cycling parameters were: 9 minutes at 95° C. followed by 45 cycles of 20 sec at 95° C., 25 sec at 55° C. and 25 sec at 72° C. For melt curve analysis the temperature was increased in 0.2° C. increments from 60 to 94° C.

Example 12

Profiling of Defined Mixtures of Live and Isopropanol-Killed Environmental Isolates Four bacterial isolates from a duck pond were randomly chosen and cultivated. Partial sequencing of cloned 16S rRNA genes allowed identification of closest phylogenetic neighbors (FIG. 10). Identical volumes of either untreated or isopropanol-killed pure cultures were mixed in defined ratios according to the pipetting scheme shown in FIG. 10. Whereas mixture I contained only untreated live cells, mixture II comprised only killed cells. The remaining mixtures comprised three live species and one killed species each. DGGE profiles obtained from partial 16S rRNA gene PCR products for non-PMA treated mixtures I-VI had four dominant bands reflecting the four isolates. PMA treatment resulted in the suppression of bands of the isopropanol-killed isolates: Whereas mixture I (only live cells) still produced four dominant bands, mixture II (only killed cells) did not produce any bands. PMA treatment of mixtures III-VI produced three dominant bands representing the three live species.

Example 13

Profiling of a WWTP Influent Sample Spiked with Defined Ratios of Live and Dead Cells Identical aliquots of a WWTP influent sample were spiked with $10^7$ cells of the human pathogen *E. coli* 0157:H7 (either untreated or heat-killed). Although the total number of *E. coli* 0157:H7 cells was constant, the spikes comprised an increasing proportion of live cells ranging from 0 to 100%. DGGE profiles from amplified 16S rRNA genes are shown in FIG. 11A. The community fingerprint of the WWTP influent sample showed six prominent bands and was not affected by PMA treatment. Each spiked sample without PMA treatment showed an additional band identical in length to the band derived from a pure *E. coli* 0157:H7 culture. Band intensities were comparable independent of the percentage of live cells. PMA treatment led to an elimination of the *E. coli* 0157:H7 signal for the samples spiked with 0, 0.1 and 1% live cells. For the PMA-treated sample spiked with 10% live cells, a faint spike band became visible. The band intensity of this pathogen signal became increasingly stronger for samples spiked with 50 and 100% live cells. The intensity of the *E. coli* 0157:H7 band of the PMA-treated sample spiked only with live cells was comparable to the intensities of the corresponding bands in the non-PMA treated samples.

The increasing visibility of the pathogen band with increasing proportions of live cells in DGGE after PMA treatment correlated with the data obtained from quantitative PCR detecting relative differences in shiga toxin 1 gene (stx1) copies (FIG. 11B). $C_t$ values obtained from PMA-treated spiked samples were subtracted from the corresponding $C_t$ values of non-PMA treated spiked samples. The obtained negative values are referred to as 'signal reduction'. Signal reduction was strongest with −12.7 cycles for the sample spiked only with dead cells. Increasing proportions of live cells resulted in decreasing qPCR signal reduction. For the sample spiked with only live cells signal reduction was minimal (−0.3 cycles), meaning PMA treatment had only a minimal effect on the quantification of stx1 gene copies.

Example 14

Profiling of Selected Environmental Microbial Communities

Figure 12:
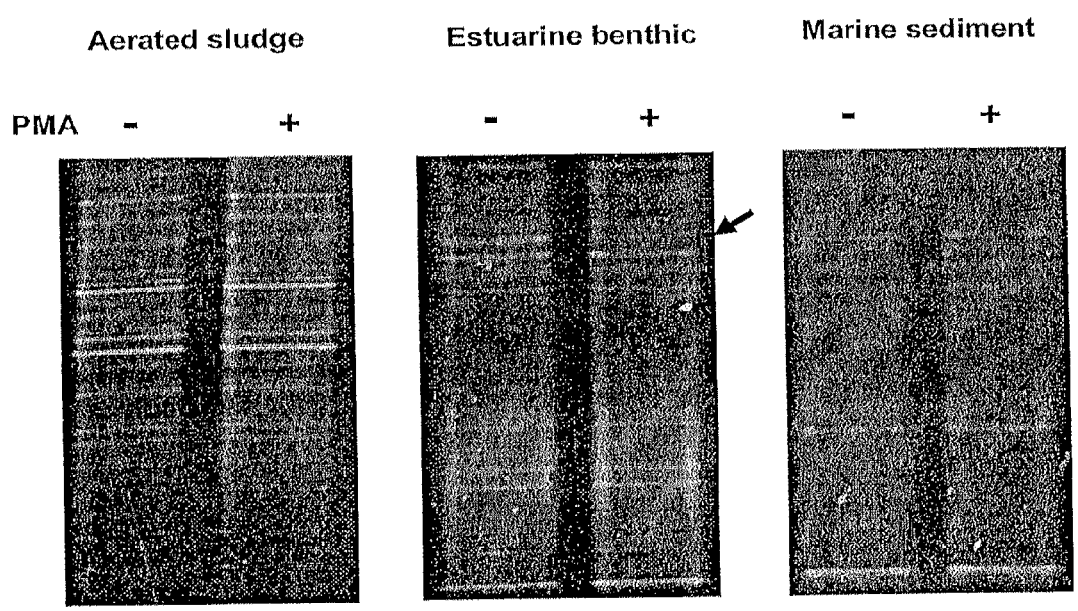
FIG. 12. DGGE profiles of amplified partial 16S rRNA genes of aerated sludge, estuarine benthic and marine sediment samples without and with prior PMA treatment. The arrow indicates a PMA-caused difference in the estuarine benthic profile.

The results from the previous experiments encouraged us to study the effect of PMA treatment on natural environmental samples. Three diverse communities were chosen: (1) A sample from an aerated sludge basin from a waste water treatment plant, (2) an estuary benthos sample and (3) a marine sediment sample. Samples were either PMA-treated or not. 16S rRNA gene-based DGGE profiles are shown in FIG. 12. The PMA treatment did not visibly change community profiles of the aerated sludge or the marine sediment sample, but there was one pronounced difference in the estuarine sample with one prominent band in the non-PMA treated sample appeared significantly weaker in the PMA treated sample.

Example 15

Profiling of a Water Reservoir Sediment Sample Exposed to Increasing Stress

Figure 13:
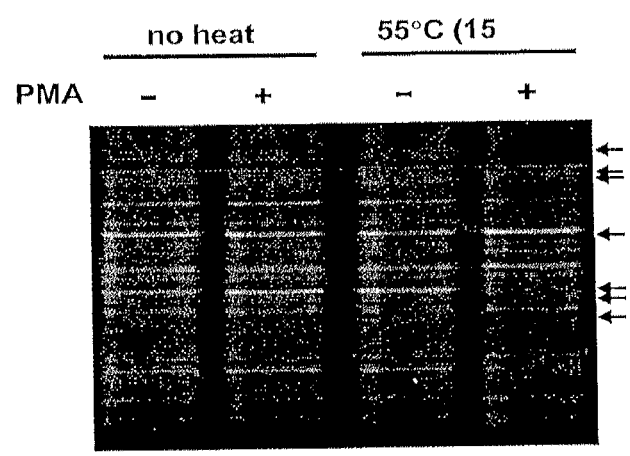
FIG. 13. DGGE profiles of amplified partial 16S rRNA genes of a water sediment sample, which was either not exposed to heat or heated at 55° C. for 15 minutes. Samples were treated with PMA or not prior DNA extraction and PCR amplification. Arrows indicate most visible differences in banding patterns.
Figure 14:
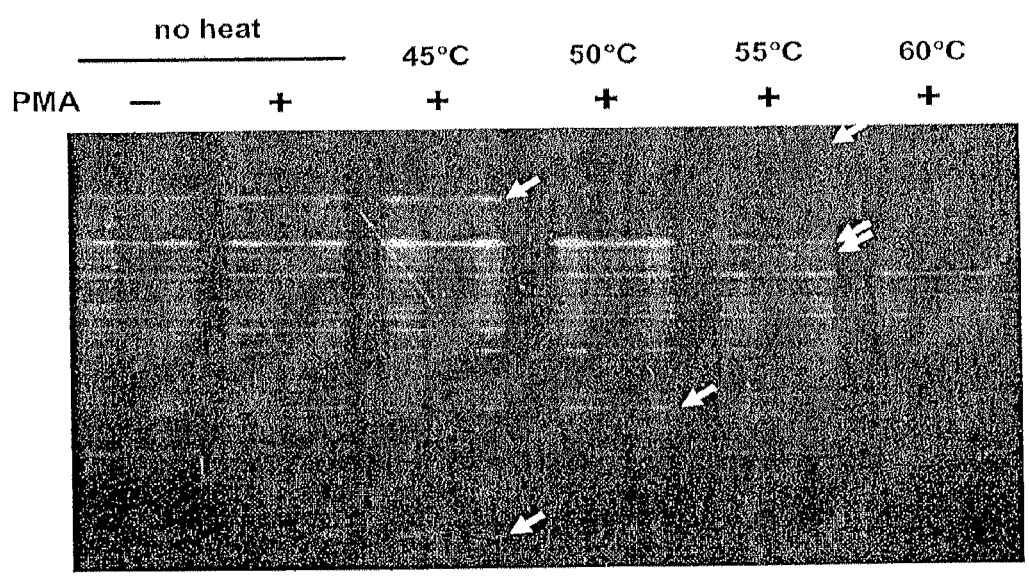
FIG. 14. DGGE profiles of amplified partial 16S rRNA genes of a water sediment sample, which was either not exposed to heat or heated at the indicated temperatures for 15 minutes. All but one sample were treated with PMA prior DNA extraction and PCR amplification. Arrows indicate bands which undergo a visible temperature-induced change in intensity in the profiles.

A water reservoir sediment sample was chosen to study whether the exposure to heat stress would affect DGGE community profiles. Aliquots of the sample were exposed to 55° C. for 15 min and either PMA-treated or not. Resulting DGGE profiles were compared with the ones from the corresponding non-heated samples (FIG. 13). Whereas PMA did not affect the fingerprint of the non-heated sample, it resulted in loss of some bands in the heat-exposed sample. To solidify this finding, another water sediment sample was exposed to a heat gradient in the range between 45 and 60° C. (for 15 minutes each) followed by PMA treatment. Exposure to 45° C. did not affect the DGGE profile compared to either a PMA-treated or non-PMA treated non-heated sample. However, increasing temperatures further resulted in increasing loss of DGGE bands.

The above experiments shows that PMA treatment can efficiently suppress signals from killed cells in defined mixtures or in an environmental sample spiked with defined mixtures of live and killed cells. It is also critical to note that although PMA treatment of samples might be a good way to exclude membrane-compromised cells from analysis. As stated earlier, limiting analysis to intact cells would be a step forward in analyzing the more relevant fraction of the total community.

Summarizing the above, this invention provides novel chemicals allowing the removal of genomic DNA from cells with compromised cell membranes. The fast and easy-to-perform pre-treatment of a bacterial population before DNA extraction is compatible with further downstream analyses. Although its application to 'real-world' samples still requires further evaluation, the method could have a great impact on DNA-based diagnostics in various fields, including pathogen diagnostics, bioterrorism and microbial ecology.

All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. Coffman, G. L., Gaubatz, J. W., Yielding, K. L. & Yielding, L. W. Demonstration of specific high affinity binding sites in plasmid DNA by photoaffinity labeling with ethidium analog. *J. Biol. Chem.* 257, 13205-13297 (1982).
2. DeTraglia, M. C., Brand, J. S. & Tometski, A. M. Characterization of azidobenzamidines as photoaffinity labeling for trypsin. *J. Biol. Chem.* 253, 1846 (1978).
3. Jernaes, M. W., & Steen, H. B. Staining of *Escherichia coli* for flow cytometry: influx and efflux of ethidium bromide. *Cytometry* 17, 302-309 (1994).
4. Josephson, K. L., Gerba, C. P. & Pepper, I. L. Polymerase chain reaction detection of nonviable bacterial pathogens. *Appl. Environ. Microbiol.* 59, 3513-3515 (1993).
5. Kell, D. B., Kaprelyants, A. S., Weichart, D. H., Harwood, C. R. & Barer, M. R. Viability and activity in readily culturable bacteria: a review and discussion of the practical issues. Antonie Van Leeuwenhoek 73, 169-187 (1998).
6. Masters, C. I., Shallcross, J. A. & Mackey, B. M. Effect of stress treatments on the detection of *Listeria monocytogenes* and enterotoxigenic *Escherichia coli* by the polymerase chain reaction. *J. Applied. Bacteriol.* 77, 73-79 (1994).
7. Morris, C. E. et al. The Relationship of Host Range, Physiology, and Genotype to Virulence on Cantaloupe in *Pseudomonas syringae* from Cantaloupe Blight Epidemics in France. *Phytopathology* 90, 636-646 (2000).
8. Nebe-von-Caron, G., Stephens, P. J., Hewitt, C. J., Powell, J. R. & Badley, R. A. Analysis of bacterial function by multi-colour fluorescence flow cytometry and single cell sorting. *J. Microbiol. Methods* 42, 97-114 (2000).
9. Nebe-von Caron, G., Stephens, P. & Badley, R. A. Assessment of bacterial viability status by flow cytometry and single cell sorting. *J. Appl. Microbiol.* 84, 988-998 (1998).
10. Nocker, A. & Camper, A. K. Selective removal of DNA from dead cells of mixed bacterial communities by use of ethidium monoazide. *Appl. Environ. Microbiol.*, in press, scheduled for March 2006, vol. 72, issue 3 (2006).
11. Nogva, H. K., Dromtorp, S. M., Nissen, H. & Rudi, K. Ethidium monoazide for DNA-based differentiation of viable and dead bacteria by 5'-nuclease PCR. *BioTechniques* 810, 812-813 (2003).
12. Rueckert, A., Ronimus, R. S. & Morgan, H. W. Rapid differentiation and enumeration of the total, viable vegetative cell and spore content of thermophilic bacilli in milk powders with reference to *Anoxybacillus flavithermus*. *J. Appl. Microbiol.* 99, 1246-1255 (2005).
13. Rudi, K., Moen, B., Dromtorp, S. M. & Holck, A. L. Use of ethidium monoazide and PCR in combination for quantification of viable and dead cells in complex samples. *Appl. Envir. Microbiol.* 71, 1018-1024 (2005).
14. Rudi, K., Naterstad, K., Dromtorp, S. M. & Holo, H. Detection of viable and dead *Listeria monocytogenes* on gouda-like cheeses by real-time PCR. *Lett. Appl. Microbiol.* 40, 301-306 (2005).
15. Shapiro, H. M., & Nebe-von-Caron, G. Multiparameter flow cytometry of bacteria. *Methods Mol. Biol.* 263, 33-44 (2004).
16. Sharma, V. K., & Dean-Nystrom, E. A. Detection of enterohemorrhagic *Escherichia coli* 0157:H7 by using a multiplex real-time PCR assay for genes encoding intimin and Shiga toxins. *Veterin. Microbiol.* 93, 247-260 (2003).
17. Waring, M. J. Complex formation between ethidium bromide and nucleic acids. *J. Mol. Biol.* 13, 269-282 (1965).
18. Camper, A. K., and McFeters, G. A. Chlorine injury and the enumeration of waterborne coliform bacteria. *Appl. Environ. Microbiol,* 37, 633-641 (1979).
19. Venkobachar, C., Iyengar, L., Rao, A., Mechanism of disinfection: effect of chlorine on cell membrane functions. *Water Res.* 11, 727-729 (1977).
20. Adair, F. W., Geftic, S. G., Gelzer, J., Resistance of *Pseudomonas* to Quaternary Ammonium Compounds. I. Growth in Benzalkonium Chloride Solution. *Appl. Environ. Microbiol.* 18, 299-302 (1969).
21. Masters, C. I., Shallcross, J. A., Mackey, B. M., Effect of stress treatments on the detection of *Listeria monocytogenes* and enterotoxigenic *Escherichia coli* by the polymerase chain reaction. *J. Applied. Bacteriol.* 77, 73-79 (1994).
22. Douki T., & Cadet, J., UV and nucleic acids. In Interface Between Chemistry and Biochemistry (Edited by H. Jürnvall and P. Jones), pp. 173-197. Birkhäuser, Basel (1995).
23. Moan J., & Peak, M. J., Effects of UV radiation on cells. *J. Photochem. Photobiol. Biol. B.* 4, 21-34 (1989).

24. Shaunivan, L. L., Delbaere, L. T. J., Lee, J. S., Gamma and Ultraviolet Radiation Cause DNA Crosslinking in the Presence of Metal Ions at High pH. *Photochemistry and Photobiology* 73, 579-584 (2001).
25. Morgan A. R., Lee, J. S., Pulleyblank, D. E., Murray, N. L., Evans, D. H., Review: ethidium fluorescence assays. Part 1. Physiochemical studies. *Nucleic Acid Res.* 7, 547-569 (1979).
26. Nocker, A., and Camper, A. K., Selective removal of DNA from dead cells of mixed bacterial communities by use of ethidium monoazide. *Appl. Environ. Microbiol.* 72, 1997-2004 (2006).
27. Nocker, A, Cheung, C Y, and Camper, A. K., Comparison of propidium monoazide with ethidium monoazide for differentiation of live vs. dead bacteria by selective removal of DNA from dead cells. *J. Microbiol. Methods* 67, 310-320 (2006).

TABLE 1

Bacterial species and growth conditions

| Species | Growth medium | Growth temperature | Strain/Origin |
|---|---|---|---|
| *E. coli* 0157:H7 | Luria Bertani | 37° C. | Strain 932 |
| *Listeria monocytogenes* | Brain Heart Infusion | 30° C. | MSU Microbiology Dept. |
| *Micrococcus luteus* | Brain Heart Infusion | 30° C. | MSU Microbiology Dept. |
| *Mycobacterium avium* | 7H9 broth - OADC | 37° C. | Strain W2001 |
| *Pseudomonas syringae* | King's B | 22° C. | Strain CC94 Tarn-et-Garonee/France (Morris et al. 2000) |
| *Salmonella typhimurium* | Luria Bertani | 30° C. | MSU Microbiology Dept. |
| *Serratia marcescens* | Brain Heart Infusion | 25° C. | MSU Microbiology Dept. |
| *Staphylococcus aureus* | Tryptic Soy Broth | 37° C. | ATCC 25923 |
| *Streptococcus sobrinus* | Brain Heart Infusion | 37° C. | ATCC 27607 |

TABLE 2

Gene targets and primers used for relative quantification of genomic DNA from the bacterial strains.

| Strain | Gene Target | | Primer name and sequence | Product Length | Reference |
|---|---|---|---|---|---|
| *Salmonella* sp | invA | invA2-F | ATTCTGGTACTAATGGTGATGATC (SEQ ID NO 4) | 288 bp | Fey et al. 2004 |
| | invA | invA2-R | GCCAGGCTATCGCCAATAAC (SEQ ID NO 5) | | |
| *Listeria* sp. | hly | lysA-F | GGGAAATCTGTCTCAGGTGATGT (SEQ ID NO 6) | 106 bp | Guilbaud et al. 2005 |
| | hly | lysA-R | CGATGATTTGAACTTCATCTTTTGC (SEQ ID NO 7) | | |
| *E. coli* 0157:H7 | stx1 | stx1-F | ACTGCAAAGACGTATGTAGATTCG (SEQ ID NO 8) | 150 bp | Sharma/Nystrom 2003 |
| | stx1 | stx1-R | ATCTATCCCTCTGACATCAACTGC (SEQ ID NO 9) | | |
| *Mycobacterium* sp. | treS | treS-F | TACGACACCACCGACCACTA (SEQ ID NO 10) | 174 bp | Geier, 2006 |
| | treS | treS-R | CGTGATCGTCAGAGTCGATG (SEQ ID NO 11) | | |

The invention claimed is:

1. A method of microbial profiling of a sample, comprising:
   a. collecting a sample;
   b. exposing said sample to a phenanthridium derivative of formula (II):

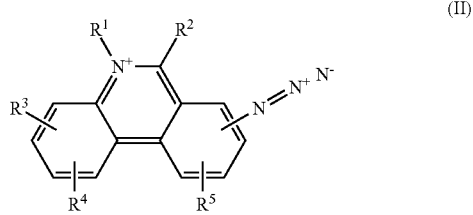

(II)

wherein
$R^1$ is an alkyl having 1 to 6 carbon atoms, perfluoroalkyl having 1 to 6 carbon atoms, or tetra-alkyl ammonium;
$R^2$ is a substituted or unsubstituted aryl, substituted or unsubstituted heteroaryl, or substituted or unsubstituted cycloalkyl having 3 to 10 carbon atoms;
$R^3$ is amino, N-alkylamino, N,N-dialkylamino, alkoxy, or carboxyalkyl; and
$R^4$ and $R^5$ are independently selected from the group consisting of: hydrogen, halide, hydroxyl, amino, N-alkylamino, N,N-dialkylamino, alkoxy, carboxyalkyl, alkyl having 1 to 6 carbon atoms, perfluoroalkyl having 1 to 6 carbon atoms, azide, and tetra-alkyl ammonium;
or a mono or bis halide salt thereof,
wherein the phenanthridium derivative has an overall charge of $2^+$ or higher;
   c. exposing said phenanthridium derivative containing sample to a light source;
   d. optionally isolating genomic DNA from said sample; and
   e. performing PCR on said isolated DNA.

2. The method of claim 1, wherein said sample is selected from the group consisting of: soil, water, sewage, food, agricultural, pharmaceuticals, and cosmetics.

3. The method of claim 1, wherein said phenanthridium derivative is PMA.

4. A method of microbial profiling of a sample comprising:
   a. collecting a sample;
   b. exposing said sample to a phenanthridium derivative of formula (II):

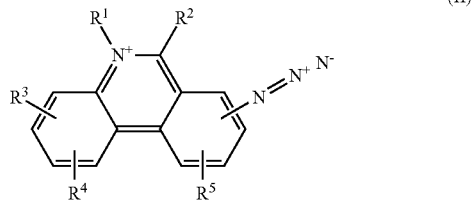

(II)

wherein
$R^1$ is an alkyl having 1 to 6 carbon atoms, perfluoroalkyl having 1 to 6 carbon atoms, or tetra-alkyl ammonium;
$R^2$ is a substituted or unsubstituted aryl, substituted or unsubstituted heteroaryl, or substituted or unsubstituted cycloalkyl having 3 to 10 carbon atoms;
$R^3$ is amino, N-alkylamino, N,N-dialkylamino, alkoxy, or carboxyalkyl; and $R^4$ and $R^5$ are independently selected from the group consisting of: hydrogen, halide, hydroxyl, amino, N-alkylamino, N,N-dialkylamino, alkoxy, carboxyalkyl, alkyl having 1 to 6 carbon atoms, perfluoroalkyl having 1 to 6 carbon atoms, azide, and tetra-alkyl ammonium;
or a mono or bis halide salt thereof,
wherein the phenanthridium derivative has an overall charge of $2^+$ or higher;
   c. exposing said phenanthridium derivative containing sample to a light source;
   d. optionally isolating RNA from said sample; and
   e. performing RT-PCR on said isolated RNA.

5. The method of claim 4, wherein said sample is selected from the group consisting of: soil, water, sewage, food, agricultural, pharmaceuticals, and cosmetics.

6. The method of claim 4, wherein said phenanthridium derivative is PMA.

7. The method of claim 1, wherein said phenanthridium derivative has a structure of formula (III):

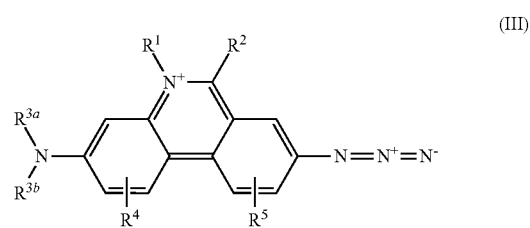

(III)

wherein
$R^1$ is an alkyl having 1 to 6 carbon atoms, perfluoroalkyl having 1 to 6 carbon atoms, or tetra-alkyl ammonium;
$R^2$ is a substituted or unsubstituted aryl, substituted or unsubstituted heteroaryl, or substituted or unsubstituted cycloalkyl having 3 to 10 carbon atoms;
$R^{3a}$ and $R^{3b}$ are independently hydrogen or alkyl having 1 to 6 carbon atoms; and
$R^4$ and $R^5$ are independently selected from the group consisting of hydrogen, halide, hydroxyl, amino, N-alkylamino, N,N-dialkylamino, alkoxy, carboxyalkyl, alkyl having 1 to 6 carbon atoms, perfluoroalkyl having 1 to 6 carbon atoms, azide, and tetra-alkyl ammonium;
or a mono or bis halide salt thereof,
wherein the phenanthridium derivative has an overall charge of $2^+$ or higher.

8. The method of claim 7, wherein said phenanthridium derivative is selected from the group consisting of: 3-amino-8-azido-5-(3-(diethylmethylammonio)propyl)-6-phenylphenanthridium diiodide, 3-amino-8-azido-5-(3-(diethylmethylammonio)propyl)-6-phenylphenanthridium dibromide, and 3-amino-8-azido-5-(3-(diethylmethylammonio)propyl)-6-phenylphenanthridium dichloride.

9. The method of claim 4, wherein said phenanthridium derivative has a structure of formula (III):

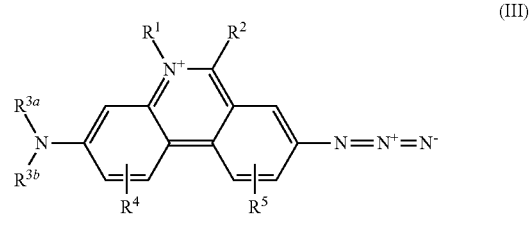

(III)

wherein
$R^1$ is an alkyl having 1 to 6 carbon atoms, perfluoroalkyl having 1 to 6 carbon atoms, or tetra-alkyl ammonium;

$R^2$ is a substituted or unsubstituted aryl, substituted or unsubstituted heteroaryl, or substituted or unsubstituted cycloalkyl having 3 to 10 carbon atoms;

$R^{3a}$ and $R^{3b}$ are independently hydrogen or alkyl having 1 to 6 carbon atoms; and $R^4$ and $R^5$ are independently selected from the group consisting of hydrogen, halide, hydroxyl, amino, N-alkylamino, N,N-dialkylamino, alkoxy, carboxyalkyl, alkyl having 1 to 6 carbon atoms, perfluoroalkyl having 1 to 6 carbon atoms, azide, and tetra-alkyl ammonium;

or a mono or bis halide salt thereof, wherein the phenanthridium derivative has an overall charge of $2^+$ or higher.

10. The method of claim 9, wherein said phenanthridium derivative is selected from the group consisting of: 3-amino-8-azido-5-(3-(diethylmethylammonio)propyl)-6-phenylphenanthridium diiodide, 3-amino-8-azido-5-(3-(diethylmethylammonio)propyl)-6-phenylphenanthridium dibromide, and 3-amino-8-azido-5-(3-(diethylmethylammonio)propyl)-6-phenylphenanthridium dichloride.

\* \* \* \* \*

SEQUENCE LISTING

<160> NUMBER OF SEQ ID NOS: 17

<210> SEQ ID NO 1
<211> LENGTH: 25
<212> TYPE: DNA
<213> ORGANISM: Escherichia coli

<400> SEQUENCE: 1
gactgcaaag acgtatgtag attcg           25

<210> SEQ ID NO 2
<211> LENGTH: 24
<212> TYPE: DNA
<213> ORGANISM: Escherichia coli

<400> SEQUENCE: 2
atctatccct ctgacatcaa ctgc            24

<210> SEQ ID NO 3
<211> LENGTH: 30

```
<212> TYPE: DNA
<213> ORGANISM: Escherichia coli

<400> SEQUENCE: 3
tgaatgtcat tcgctctgca ataggtactc                              30

<210> SEQ ID NO 4
<211> LENGTH: 24
<212> TYPE: DNA
<213> ORGANISM: Salmonella typhimurium

<400> SEQUENCE: 4
attctggtac taatggtgat gatc                                    24

<210> SEQ ID NO 5
<211> LENGTH: 20
<212> TYPE: DNA
<213> ORGANISM: Salmonella typhimurium

<400> SEQUENCE: 5
gccaggctat cgccaataac                                         20

<210> SEQ ID NO 6
<211> LENGTH: 23
<212> TYPE: DNA
<213> ORGANISM: Listeria monocytogenes

<400> SEQUENCE: 6
gggaaatctg tctcaggtga tgt                                     23

<210> SEQ ID NO 7
<211> LENGTH: 25
<212> TYPE: DNA
<213> ORGANISM: Listeria monocytogenes

<400> SEQUENCE: 7
cgatgatttg aacttcatct tttgc                                   25

<210> SEQ ID NO 8
<211> LENGTH: 24
<212> TYPE: DNA
<213> ORGANISM: Escherichia coli

<400> SEQUENCE: 8
actgcaaaga cgtatgtaga ttcg                                    24

<210> SEQ ID NO 9
<211> LENGTH: 24
<212> TYPE: DNA
<213> ORGANISM: Escherichia coli

<400> SEQUENCE: 9
atctatccct ctgacatcaa ctgc                                    24

<210> SEQ ID NO 10
<211> LENGTH: 20
<212> TYPE: DNA
<213> ORGANISM: Mycobacterium avium

<400> SEQUENCE: 10
tacgacacca ccgaccacta                                         20

<210> SEQ ID NO 11
```

```
<211> LENGTH: 20
<212> TYPE: DNA
<213> ORGANISM: Mycobacterium avium

<400> SEQUENCE: 11
cgtgatcgtc agagtcgatg                                                    20

<210> SEQ ID NO 12
<211> LENGTH: 16
<212> TYPE: DNA
<213> ORGANISM: Escherichia coli

<400> SEQUENCE: 12
atggctgtcg tcagct                                                        16

<210> SEQ ID NO 13
<211> LENGTH: 15
<212> TYPE: DNA
<213> ORGANISM: Escherichia coli

<400> SEQUENCE: 13
acgggcggtg tgtac                                                         15

<210> SEQ ID NO 14
<211> LENGTH: 40
<212> TYPE: DNA
<213> ORGANISM: Artificial Sequence
<220> FEATURE:
<223> OTHER INFORMATION: PCR primer targeted to plasmid containing a
      designed GC clamp region for enhanced hybridization

<400> SEQUENCE: 14
cgcccgccgc gccccgcgcc cggcccgccg ccccccgcccc                              40

<210> SEQ ID NO 15
<211> LENGTH: 20
<212> TYPE: DNA
<213> ORGANISM: Escherichia coli

<400> SEQUENCE: 15
agagtttgat cctggctcag                                                    20

<210> SEQ ID NO 16
<211> LENGTH: 16
<212> TYPE: DNA
<213> ORGANISM: Escherichia coli

<400> SEQUENCE: 16
acggggcggt gtgtac                                                        16

<210> SEQ ID NO 17
<211> LENGTH: 16
<212> TYPE: DNA
<213> ORGANISM: Enterobacteria phage M13

<400> SEQUENCE: 17
gtaaaacgac ggccag                                                        16
```